United States Patent
Yanaka et al.

[11] Patent Number: 5,863,913
[45] Date of Patent: Jan. 26, 1999

[54] AROMATIC COMPOUND AND PHARMACEUTICAL COMPOSITION

[75] Inventors: Mikiro Yanaka, Chiba; Hiroyuki Enari, Tokyo; Toru Yamazaki, Tokyo; Hiroshi Maruoka, Tokyo; Toshikazu Dewa, Tokyo; Fuyuhiko Nishijima, Tokyo; Hiroshi Takahashi, Fukushima; Michihito Ise, Saitama, all of Japan

[73] Assignee: Kureha Chemical Industry Co., Ltd., Tokyo, Japan

[21] Appl. No.: 857,206

[22] Filed: May 15, 1997

[30] Foreign Application Priority Data

May 17, 1996 [JP] Japan .................................. 8-148382

[51] Int. Cl.$^6$ .................... A61K 31/44; A61K 31/535; C07D 411/06; C07D 295/192
[52] U.S. Cl. .................... 514/227.5; 514/227.8; 514/235.5; 514/237.5; 514/255; 514/318; 514/330; 514/343; 514/423; 514/533; 514/539; 514/563; 514/567; 544/58.4; 544/131; 544/165; 544/365; 544/391; 546/194; 546/276; 546/279.1; 546/307; 546/309; 548/539; 560/48; 562/457
[58] Field of Search ............... 514/227.5, 237.5, 514/255, 330, 423, 563, 227.8, 235.5, 318, 343, 533, 539, 567; 544/165, 391, 58.4, 131, 365; 546/226, 194, 279.1, 307, 309; 548/539; 560/48; 562/457

[56] References Cited

U.S. PATENT DOCUMENTS 5,696,118 12/1997 Yanaka et al. .................... 514/237.5

FOREIGN PATENT DOCUMENTS 685470 12/1995 European Pat. Off. .

OTHER PUBLICATIONS

Wyngaarden, J.B. et al, Cecil Textbook of Medicine, 19th edition, W.B. Saunders Co., 1992, pp. 556–557.

*Primary Examiner*—Richard L. Raymond
*Attorney, Agent, or Firm*—Sughrue, Mion, Zinn, Macpeak & Seas, PLLC

[57] ABSTRACT

An aromatic compound of the formula (I):

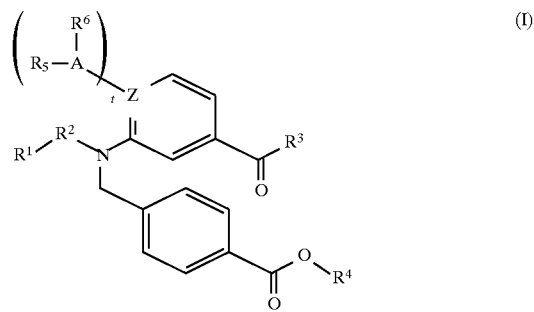

specifically, for example, 3-[[(4-carboxyphenyl)methyl] valeramido]-4-dimethylaminobenzoic acid 4'-methylpiperazide, or a salt thereof, and a pharmaceutical composition comprising said aromatic compound or pharmaceutically acceptable salt thereof, and a pharmaceutically acceptable carrier or diluent which provides sufficiently effective alleviation of renal dysfunction without affecting blood pressure at a low blood concentration.

9 Claims, No Drawings

AROMATIC COMPOUND AND PHARMACEUTICAL COMPOSITION

BACKGROUND OF THE INVENTION

1. Field of the Invention

The present invention relates to a novel aromatic compound or a salt thereof, and a pharmaceutical composition, particularly, an agent, for treating a kidney disease, containing said aromatic compound or a pharmaceutically acceptable salt thereof.

2. Description of the Related Art

There is now an increasing number of patients suffering from renal dysfunction. This is believed to be because a development of drugs appropriate to the treatment of kidney diseases has lagged behind with an increase in the number of senior citizens in the population or with changes in the environment. Therefore, drugs appropriate to the treatment of kidney diseases are urgently required.

More particularly, a method for treating lesions accompanying diseases, i.e., a nosotropic treatment, is mainly used for kidney diseases such as nephritis, diabetic nephropathy or renal failure. For example, an antihypertensive, diuretic or anti-inflammatory agent, or a dietary treatment, kinesitherapy or the like is used. Because kidney diseases are accompanied by hypertension, and because hypertension is believed to be one of the factors that aggravate kidney diseases, antihypertensive agents are often used. Of the antihypertensive agents, those that inhibit the production or function of angiotensin II are used in many cases. This is because angiotensin II is believed to be a factor aggravating kidney diseases as it raises the blood pressure and accelerates the growth of interstitial cells in the kidney, and an elimination of such a factor, insofar as possible, is believed to alleviate kidney diseases.

Specifically, the agents for inhibiting the enzyme which converts angiotensin I to angiotensin II, which raises the blood pressure, for example, the angiotensin converting enzyme inhibitor (such as enalapril or captoril) or the angiotensin II receptor antagonist (such as Dup753 or MK954), were developed as an antihypertensive agent for the treatment of kidney diseases.

In kidney diseases, the hypertension is an important symptom to be alleviated. A mere lowering of the blood pressure, however, is not sufficient. It is important to maintain an appropriate blood pressure, and thus, it is necessary to adjust the blood pressure by combining the kinds and doses of the antihypertensive agents in accordance with the symptoms. Nevertheless, a continuous treatment with a sufficient dose is required for the kidney diseases per se. Therefore, as long as a conventional antihypertensive agent is used, it is fundamentally impossible to appropriately adjust the blood pressure, and at the same time, to effectively cure a kidney disease by the antihypertensive agent alone. One such problem is, for example, an acute renal failure caused by the antihypertensive agent used.

Japanese Unexamined Patent Publication (Kokai) No. 8-48651 discloses compounds having novel properties, namely compounds providing a sufficiently effective alleviation of the renal dysfunction without any function to the blood pressure. These compounds are aromatic compounds which provide a sufficient effect in the alleviation of the renal dysfunction while the antagonism thereof to the angiotensin II receptor subtype 1 is one-hundredth (1/100) to one-thousandth (1/1000) or less that of the conventional antagonist having a standard activity as a antihypertensive agent.

SUMMARY OF THE INVENTION

The inventors of the present invention carried out intensive studies into the development of different compounds having properties that are the same as those of the compounds disclosed in the above Japanese Unexamined Patent Publication (Kokai) No. 8-48651, and as a result, found novel compounds which provide a sufficiently effective alleviation of the renal dysfunction without any function to the blood pressure as the compound disclosed in Japanese Unexamined Patent Publication (Kokai) No. 8-48651, and further exhibit an improved behavior at a blood concentration in comparison with the compound disclosed in Japanese Unexamined Patent Publication (Kokai) No. 8-48651. The present invention is based on this finding.

Accordingly, the object of the present invention is to provide a novel compound providing a sufficiently effective alleviation of the renal dysfunction while not affecting the blood pressure.

Other objects and advantages will be apparent from the following description.

In accordance with the present invention, there is provided an aromatic compound of the formula (I):

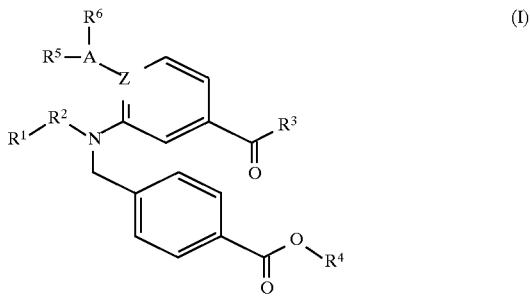

wherein $R^1$ is a hydrogen atom, an alkyl of 1 to 8 carbon atoms, a haloalkyl of 1 to 8 carbon atoms, or —$NR^7R^8$; $R^2$ is —C(=O)— or a single bond; $R^3$ is —$OR^9$, a three- to seven-membered saturated cycloaliphatic amino group which may be interrupted by one or more nitrogen, oxygen, or sulfur atoms, a three- to seven-membered saturated cycloaliphatic amino group containing at least one nitrogen atom in the ring which is substituted with one or more alkyl groups of 1 to 8 carbon atoms or one or more haloalkyl groups of 1 to 8 carbon atoms, a three- to seven-membered saturated cycloaliphatic alkyl group containing at least one nitrogen atom in the ring which may be substituted with one or more alkyl groups of 1 to 8 carbon atoms or one or more haloalkyl groups of 1 to 8 carbon atoms, or —$NR^{10}R^{11}$;

$R^4$ is a hydrogen atom, an alkyl of 1 to 8 carbon atoms, a haloalkyl of 1 to 8 carbon atoms, —$(CH_2)_mNR^{12}R^{13}$, —$(CH_2)_nR^{14}$, —$(CH_2)_pCH(NR^{15}R^{16})COOR^{17}$, —$R^{18}$—$COOR^{19}$, —$CH(R^{20})OC(=O)OR^{21}$, or —$CH(R^{22})OC(=O)R^{23}$; $R^{10}$ and $R^{11}$ are independently a hydrogen atom, an alkyl of 1 to 8 carbon atoms, a haloalkyl of 1 to 8 carbon atoms, or —$(CH_2)_qNR^{24}R^{25}$; $R^{14}$ is a three- to seven-membered saturated cycloaliphatic amino group which may be interrupted by one or more nitrogen, oxygen, or sulfur atoms, a three- to seven-membered saturated cycloaliphatic amino group containing at least one nitrogen atom in the ring which is substituted with one or more alkyl groups of 1 to 8 carbon atoms or one or more haloalkyl groups of 1 to 8 carbon atoms, a three- to seven-membered saturated cycloaliphatic alkyl group containing at least one nitrogen atom in the ring which may be substituted with one or more alkyl groups of 1 to 8 carbon atoms or one or more haloalkyl groups of 1 to 8 carbon atoms, or a three- to seven-membered unsaturated heterocyclic group; $R^{18}$ is a three- to seven-membered saturated cycloaliphatic alkylene group containing at least one nitrogen atom in the ring which may be substituted with one or more alkyl groups of 1 to 8 carbon atoms or one or more haloalkyl groups of 1 to 8 carbon atoms; $R^{21}$ and $R^{23}$ are —$(CH_2)_r R^{26}$; $R^{26}$ is a hydrogen atom, an alkyl of 1 to 8 carbon atoms, a haloalkyl of 1 to 8 carbon atoms, —$NR^{27}R^{28}$, or a three- to eight-membered saturated cycloaliphatic alkyl group; Z is C, CH, or N; A is CH or N; $R^5$, $R^6$, $R^7$, $R^8$, $R^9$, $R^{12}$, $R^{13}$, $R^{15}$, $R^{16}$, $R^{17}$, $R^{19}$, $R^{20}$, $R^{22}$, $R^{24}$, $R^{25}$, $R^{27}$, and $R^{28}$ are independently a hydrogen atom, an alkyl of 1 to 8 carbon atoms, or a haloalkyl of 1 to 8 carbon atoms; and m, n, p, q, and r are independently 0 or an integer of 1 to 6, with the proviso that when $R^4$ is a hydrogen atom, an alkyl of 1 to 8 carbon atoms, or a haloalkyl of 1 to 8 carbon atoms, $R^3$ is a three- to seven-membered saturated cycloaliphatic amino group containing at least one nitrogen atom in the ring which is substituted with one or more alkyl groups of 1 to 8 carbon atoms or one or more haloalkyl groups of 1 to 8 carbon atoms, a three- to seven-membered saturated cycloaliphatic alkyl group containing at least one nitrogen atom in the ring which may be substituted with one or more alkyl groups of 1 to 8 carbon atoms or one or more haloalkyl groups of 1 to 8 carbon atoms, or —$NR^{10}R^{11}$ wherein at least one of $R^{10}$ and $R^{11}$ is —$(CH_2)_q NR^{24}R^{25}$, or a salt thereof.

Further, in accordance with the present invention, there is provided a pharmaceutical composition comprising the aromatic compound of the formula (I) or a pharmaceutically acceptable salt thereof, and a pharmaceutically acceptable carrier or diluent, particularly, an agent for treating kidney diseases.

Still further, in accordance with the present invention, there is provided a method for treating kidney diseases, comprising administering to a mammal in need thereof an effective amount of the aromatic compound of the formula (I) or a pharmaceutically acceptable salt thereof.

Still further, in accordance with the present invention, there is provided a use of the aromatic compound of the formula (I) or a pharmaceutically acceptable salt thereof in the preparation of a pharmaceutical composition.

DETAILED DESCRIPTION OF THE PREFERRED EMBODIMENTS

The term "alkyl" as used herein includes straight-chain and branched alkyl groups, for example, an alkyl group of 1 to 5 carbon atoms, such as methyl, ethyl, n-propyl, i-propyl, n-butyl, i-butyl, s-butyl, t-butyl, n-pentyl, i-pentyl, neopentyl, t-pentyl, 1-methylbutyl, 2-methylbutyl, 1,2-dimethylpropyl, or 1-ethylpropyl; an alkyl group of 1 to 6 carbon atoms, such as those as mentioned above, n-hexyl, i-hexyl, or 2-ethylbutyl; and an alkyl group of 1 to 8 carbon atoms, such as those as mentioned above, n-heptyl, 5-methylhexyl, n-octyl, or 4-ethylhexyl.

The haloalkyl group of 1 to 8 carbon atoms is the above alkyl group of 1 to 8 carbon atoms substituted with 1 to 17 halogen atoms. The halogen atom is, for example, a chlorine, bromine, fluorine, or iodine atom. The preferred haloalkyl group is, for example, a trifluoromethyl, pentafluoroethyl, or 4,4,4-trifluorobutyl.

The three- to seven-membered saturated cycloaliphatic amino group which may be interrupted by one or more nitrogen, oxygen, or sulfur atoms is an alkyleneamino group which may be optionally interrupted by a heteroatom such as a nitrogen, oxygen, or sulfur atom, for example, 1-aziridinyl, 1-azetidinyl, 1-pyrrolidinyl, piperidino, morpholino, thiomorpholino, 1-piperazinyl, 1-imidazolidinyl, 1-pyrazolidinyl group.

The three- to seven-membered saturated cycloaliphatic amino group containing at least one nitrogen atom in the ring which is substituted with one or more (preferably one) alkyl groups of 1 to 8 carbon atoms or one or more (preferably one) haloalkyl group of 1 to 8 carbon atoms is, for example, 4-methylpiperazin-1-yl, 4-ethylpiperazin-1-yl, 4-propylpiperazin-1-yl, 4-butylpiperazin-1-yl, 4-pentylpiperazin-1-yl, 4-hexylpiperazin-1-yl, 3-methylimidazolidin-1-yl, 2-methylpyrazolidin-1-yl, 4-trifluoromethylpiperazin-1-yl, or 4-trifluoroethylpiperazin-1-yl group.

The three- to seven-membered saturated cycloaliphatic alkyl group containing at least one nitrogen atom in the ring which may be substituted with one or more (preferably one) alkyl groups of 1 to 8 carbon atoms or one or more (preferably one) haloalkyl group of 1 to 8 carbon atoms is, for example, 1-methylaziridinyl, 1-methylazetidinyl, 1-methylpyrrolidinyl, 1-ethylpyrrolidinyl, 1-propylpyrrolidinyl, pyrrolidinyl, 3-methylimidazolidin-4-yl, 1-methylpyrazolidin-4-yl, piperidinyl, 1-methylpiperidinyl, 1-ethylpiperidinyl, 1-propylpiperidinyl, 1-trifluoromethylpyrrolidinyl, 1-trifluoroethylpyrrolidinyl, 1-trifluoromethylpiperidyl, or 1-trifluoroethylpiperidyl group.

The three- to seven-membered unsaturated heterocyclic group is a group of a three- to seven-membered heterocyclic compound containing 1 to 7 heteroatoms, such as a nitrogen, oxygen, or sulfur atom, for example, imidazolyl, oxazolyl, thiazolyl, pyrazolyl, isoxazolyl, isothiazolyl, triazolyl, oxadiazolyl, thiadiazolyl, tetrazolyl, oxatriazolyl, thiatriazolyl, thienyl, furyl, pyranyl, pyrrolyl, pyrazolinyl, imidazolinyl, pyridyl, pyrazinyl, pyrimidinyl, or pyridazinyl group.

The three- to seven-membered saturated cycloaliphatic alkylene group containing at least one nitrogen atom in the ring which may be substituted with one or more (preferably one) alkyl groups of 1 to 8 carbon atoms or one or more (preferably one) haloalkyl group of 1 to 8 carbon atoms is a three- to seven-membered saturated cycloaliphatic alkylene group which may be optionally substituted with one or more (preferably one) alkyl groups of 1 to 8 carbon atoms or one or more (preferably one) haloalkyl group of 1 to 8 carbon atoms and contains at least one nitrogen atom in the ring, for example, 1-methylaziridinylene, 1-methylazetidinylene, 1-methylpyrrolidinylene, 1-ethylpyrrolidinylene, 1-propylpyrrolidinylene, pyrrolidinylene, 3-methylimidazolidin-4-ylene, 1-methylpyrazolidin-4-ylene, piperidinylene, 1-methylpiperidinylene, 1-ethylpiperidinylene, 1-propylpiperidinylene, 1-trifluoromethylpyrrolidinylene, 1-trifluoroethylpyrrolidinylene, 1-trifluoromethylpiperidinylene, or 1-trifluoroethylpiperidinylene.

The three- to eight-membered saturated cycloaliphatic alkyl group is, for example, cyclopropyl, cyclobutyl, cyclopentyl, cyclohexyl, cycloheptyl, or cyclooctyl group.

The aromatic compound of the formula (I) wherein $R^1$ is a hydrogen atom, an alkyl of 1 to 8 carbon atoms, a haloalkyl of 1 to 8 carbon atoms, or —$NR^7R^8$; $R^2$ is —$C(=O)$— or single bond; $R^3$ is —$OR^9$, a three- to six-membered saturated cycloaliphatic amino group which may be interrupted by one or more nitrogen, oxygen, or sulfur atoms, a three- to six-membered saturated cycloaliphatic amino group containing at least one nitrogen atom in the ring which is substituted with one or more alkyl groups of 1 to 6 carbon atoms or one or more haloalkyl groups of 1 to 6 carbon atoms, a three- to six-membered saturated cycloaliphatic alkyl group containing at least one nitrogen atom in the ring which may be substituted with one or more alkyl groups of 1 to 6 carbon atoms or one or more haloalkyl groups of 1 to 6 carbon atoms, or —$NR^{10}R^{11}$; $R^4$ is a hydrogen atom, an alkyl of 1 to 5 carbon atoms, a haloalkyl of 1 to 5 carbon atoms, —$(CH_2)_m NR^{12}R^{13}$, —$(CH_2)_n R^{14}$, —$(CH_2)_p CH(NR^{15}R^{16})COOR^{17}$, —$R^{18}$—$COOR^{19}$, —$CH(R^{20})OC(=O)OR^{21}$, or —$CH(R^{22})OC(=O)R^{23}$; $R^{10}$ and $R^{11}$ is independently a hydrogen atom, an alkyl of 1 to 5 carbon atoms, a haloalkyl of 1 to 5 carbon atoms, or —$(CH_2)_q NR^{24}R^{25}$; $R^{14}$ is a three- to six-membered saturated cycloaliphatic amino group which may be interrupted by one or more nitrogen, oxygen, or sulfur atoms, a three- to six-membered saturated cycloaliphatic amino group containing at least one nitrogen atom in the ring which is substituted with one or more alkyl groups of 1 to 6 carbon atoms or one or more haloalkyl groups of 1 to 6 carbon atoms, a three- to six-membered saturated cycloaliphatic alkyl group containing at least one nitrogen atom in the ring which may be substituted with one or more alkyl groups of 1 to 6 carbon atoms or one or more haloalkyl groups of 1 to 6 carbon atoms, or a three- to six-membered unsaturated heterocyclic group; $R^{18}$ is a three- to six-membered saturated cycloaliphatic alkylene group containing at least one nitrogen atom in the ring which may be substituted with one or more alkyl groups of 1 to 6 carbon atoms or one or more haloalkyl groups of 1 to 6 carbon atoms; $R^{21}$ and $R^{23}$ is —$(CH_2)_r R^{26}$; $R^{26}$ is a hydrogen atom, an alkyl of 1 to 5 carbon atoms, a haloalkyl of 1 to 5 carbon atoms, —$NR^{27}R^{28}$, or a three- to six-membered saturated cycloaliphatic alkyl group; Z is C, CH, or N; A is CH or N; $R^5$, $R^6$, $R^7$, $R^8$, $R^9$, $R^{12}$, $R^{13}$, $R^{15}$, $R^{16}$, $R^{17}$, $R^{19}$, $R^{20}$, $R^{22}$, $R^{24}$, $R^{25}$, $R^{27}$, and $R^{28}$ are independently a hydrogen atom, an alkyl of 1 to 5 carbon atoms, or a haloalkyl of 1 to 5 carbon atoms; m, n, p, q, and r is independently 0 or an integer of 1 to 4, with the proviso that when $R^4$ is a hydrogen atom, an alkyl of 1 to 5 carbon atoms, or a haloalkyl of 1 to 5 carbon atoms, $R^3$ is a three- to six-membered saturated cycloaliphatic amino group containing at least one nitrogen atom in the ring which is substituted with one or more alkyl groups of 1 to 6 carbon atoms or one or more haloalkyl groups of 1 to 6 carbon atoms, a three- to six-membered saturated cycloaliphatic alkyl group containing at least one nitrogen atom in the ring which may be substituted with one or more alkyl groups of 1 to 6 carbon atoms or one or more haloalkyl groups of 1 to 6 carbon atoms, or —$NR^{10}R^{11}$ wherein at least one of $R^{10}$ and $R^{11}$ is —$(CH_2)_q NR^{24}R^{25}$, or a salt thereof, is preferable.

Further, the aromatic compound of the formula (I) wherein $R^3$ is a three- to six-membered saturated cycloaliphatic amino group containing at least one nitrogen atom in the ring which is substituted with one or more alkyl groups of 1 to 6 carbon atoms or one or more haloalkyl groups of 1 to 6 carbon atoms, a three- to six-membered saturated cycloaliphatic alkyl group containing at least one nitrogen atom in the ring which may be substituted with one or more alkyl groups of 1 to 6 carbon atoms or one or more haloalkyl groups of 1 to 6 carbon atoms, or —$NR^{10}R^{11}$ wherein at least one of $R^{10}$ and $R^{11}$ is —$(CH_2)_q NR^{24}R^{25}$, or a salt thereof is more preferable.

Alternatively, the aromatic compound of the formula (I) wherein $R^4$ is —$(CH_2)_m NR^{12}R^{13}$, —$(CH_2)_n R^{14}$, —$(CH_2)_p CH(NR^{15}R^{16})COOR^{17}$, —$R^{18}$—$COOR^{19}$, —$CH(R^{20})OC(=O)OR^{21}$, or —$CH(R^{22})OC(=O)R^{23}$, or a salt thereof, is more preferable.

The salt of the aromatic compound of the present invention includes a salt with an inorganic or organic acid or a salt with an inorganic or organic base, preferably a pharmaceutically acceptable salt. As an acid additive salt, there may be mentioned, for example, hydrochloride, sulfate, methanesulfonate or p-toluenesulfonate; a salt with a dicarboxylic acid, such as oxalic, malonic, succinic, maleic or fumaric acid; or a salt with a monocarboxylic acid, such as acetic, propionic or butyric acid. The inorganic base suitable to form a salt of the compound of the present invention is, for example, a hydroxide, carbonate or bicarbonate of ammonium, sodium, lithium, calcium, magnesium or aluminum. As the salt with the organic base, there may be mentioned, for example, a salt with a mono-, di- or trialkylamine, such as methylamine, dimethylamine or triethylamine; a salt with a mono-, di- or trihydroxyalkylamine, guanidine, N-methylglucosamine or amino acid salt.

The more particularly preferable salt of the aromatic compound of the present invention is an acid additive salt which is formed together with one or more nitrogen atoms in the following cases (a) to (c):

(a) when $R^3$ is a three- to seven-membered saturated cycloaliphatic amino group containing at least one nitrogen atom in the ring which is substituted with one or more alkyl groups of 1 to 8 carbon atoms or one or more haloalkyl groups of 1 to 8 carbon atoms, a three- to seven-membered saturated cycloaliphatic alkyl group containing at least one nitrogen atom in the ring which may be substituted with one or more alkyl groups of 1 to 8 carbon atoms or one or more haloalkyl groups of 1 to 8 carbon atoms, or —$NR^{10}R^{11}$ wherein at least one of $R^{10}$ and $R^{11}$ is —$(CH_2)_q NR^{24}R^{25}$;

(b) when a three- to seven-membered saturated cycloaliphatic amino group containing at least one nitrogen atom in the ring which is substituted with one or more alkyl groups of 1 to 8 carbon atoms or one or more haloalkyl groups of 1 to 8 carbon atoms, a three- to seven-membered saturated cycloaliphatic alkyl group containing at least one nitrogen atom in the ring which may be substituted with one or more alkyl groups of 1 to 8 carbon atoms or one or more haloalkyl groups of 1 to 8 carbon atoms, or a three- to seven-membered unsaturated heterocyclic group containing at least one nitrogen atom; or (c) when $R^{18}$ is a three- to seven-membered saturated cycloaliphatic alkylene group containing at least one nitrogen atom in the ring which may be substituted with one or more alkyl groups of 1 to 8 carbon atoms or one or more haloalkyl groups of 1 to 8 carbon atoms.

As a typical example of the aromatic compound of the present invention, the structures of Compounds No. 1 to No. 87 are shown in the following Table 1. The compounds listed in the Table 1 will be sometimes identified by the numbers given in the Table 1.

In the following Table, Me is methyl, Et is ethyl, Pr is propyl, Bu is butyl, Hex is hexyl, Hep is heptyl, $NC_4H_8O$ is morpholino, $NC_4H_8NR$ wherein R is an alkyl is 4-alkylpiperazin-1-yl, $cycC_4H_6NH$ is pyrrolidinylene, $NC_4H_8$ is 1-pyrrolidinyl, $NC_5H_{10}$ is piperidino, $NC_4H_8S$ is thiomorpholino, and $NC_4H_8NH$ is 1-piperazinyl.

TABLE 1

| No. | R¹ | A | Z | R² | R³ | R⁴ | R⁵ | R⁶ |
|---|---|---|---|---|---|---|---|---|
| 1 | nBu | N | C | CO | $NC_4H_8O$ | $CH_2CH_2NMe_2$ | Me | Me |
| 2 | nBu | N | C | CO | $NC_4H_8O$ | $CH_2CH_2CH_2NMe_2$ | Me | Me |
| 3 | nBu | N | C | CO | $NC_4H_8O$ | $CH_2CH_2CH_2NH_2$ | Me | Me |
| 4 | nBu | N | C | CO | $NC_4H_8O$ | $CH_2CH(CO_2Et)NH_2$ | Me | Me |
| 5 | nBu | N | C | CO | $NC_4H_8O$ | $cycC_4H_6NH(CO_2Et)$ | Me | Me |
| 6 | nBu | CH | C | CO | $NC_4H_8O$ | $CH_2CH_2NMe_2$ | Me | Me |
| 7 | nBu | CH | C | CO | $NC_4H_8O$ | $CH_2CH_2CH_2NMe_2$ | Me | Me |
| 8 | nBu | CH | C | CO | $NC_4H_8O$ | $CH_2CH_2NEt_2$ | Me | Me |
| 9 | nBu | CH | C | CO | $NC_4H_8O$ | $CH_2CH_2NC_4H_8O$ | Me | Me |
| 10 | nBu | N | C | CO | $NC_4H_8NMe$ | H | Me | Me |
| 11 | nBu | N | C | CO | $NC_4H_8NnPr$ | H | Me | Me |
| 12 | nHex | N | C | CO | $NC_4H_8NnPr$ | H | Me | Me |
| 13 | nHex | N | C | CO | $NC_4H_8NMe$ | H | Me | Me |
| 14 | nHep | N | C | CO | $NC_4H_8NMe$ | H | Me | Me |
| 15 | nBu | CH | C | CO | $NC_4H_8NMe$ | H | Me | Me |
| 16 | nBu | CH | C | CO | $NC_4H_8NMe$ | Et | Me | Me |
| 17 | nBu | N | C | CO | $N(Et)CH_2CH_2NEt_2$ | H | Me | Me |
| 18 | nHex | CH | C | CO | $NC_4H_8NMe$ | H | Me | Me |
| 19 | nBu | CH | C | CO | $NC_4H_8NnPr$ | H | Me | Me |
| 20 | nHex | CH | C | CO | $NC_4H_8NnPr$ | H | Me | Me |
| 21 | Et | N | C | CO | $NC_4H_8O$ | $CH_2CH_2NMe_2$ | Me | Me |
| 22 | nPr | N | C | CO | $NC_4H_8O$ | $CH_2CH_2NMe_2$ | Me | Me |
| 23 | nPen | N | C | CO | $NC_4H_8O$ | $CH_2CH_2NMe_2$ | Me | Me |
| 24 | nHex | N | C | CO | $NC_4H_8O$ | $CH_2CH_2NMe_2$ | Me | Me |
| 25 | nBu | N | C | CO | $NC_4H_8O$ | $CH_2CH_2NEt_2$ | Me | Me |
| 26 | nBu | N | C | CO | $NC_4H_8O$ | $CH_2CH_2NMe_2$ | Et | Et |
| 27 | nBu | N | C | CO | $NC_4H_8$ | $CH_2CH_2NMe_2$ | Me | Me |
| 28 | nBu | N | C | CO | $NC_5H_{10}$ | $CH_2CH_2NMe_2$ | Me | Me |
| 29 | nBu | N | C | CO | $NC_4H_8S$ | $CH_2CH_2NMe_2$ | Me | Me |
| 30 | nBu | N | C | CO | $NC_4H_8NH$ | $CH_2CH_2NMe_2$ | Me | Me |
| 31 | nBu | N | C | CO | $NC_4H_8NMe$ | $CH_2CH_2NMe_2$ | Me | Me |
| 32 | Et | N | C | CO | $NC_4H_8NH$ | $CH_2CH_2NMe_2$ | Me | Me |
| 33 | Et | N | C | CO | $NC_4H_8NMe$ | $CH_2CH_2NMe_2$ | Me | Me |
| 34 | Et | N | C | CO | $NC_4H_8NnPr$ | $CH_2CH_2NMe_2$ | Me | Me |
| 35 | nPr | N | C | CO | $NC_4H_8NH$ | $CH_2CH_2NMe_2$ | Me | Me |
| 36 | nPr | N | C | CO | $NC_4H_8NMe$ | $CH_2CH_2NMe_2$ | Me | Me |
| 37 | nPr | N | C | CO | $NC_4H_8NnPr$ | $CH_2CH_2NMe_2$ | Me | Me |
| 38 | nHex | N | C | CO | $NC_4H_8NH$ | $CH_2CH_2NMe_2$ | Me | Me |
| 39 | nHex | N | C | CO | $NC_4H_8NMe$ | $CH_2CH_2NMe_2$ | Me | Me |
| 40 | nHex | N | C | CO | $NC_4H_8NnPr$ | $CH_2CH_2NMe_2$ | Me | Me |
| 41 | Et | N | C | CO | $NC_4H_8O$ | $CH_2CH_2CH_2NMe_2$ | Me | Me |
| 42 | nPr | N | C | CO | $NC_4H_8O$ | $CH_2CH_2CH_2NMe_2$ | Me | Me |
| 43 | nPen | N | C | CO | $NC_4H_8O$ | $CH_2CH_2CH_2NMe_2$ | Me | Me |
| 44 | nHex | N | C | CO | $NC_4H_8O$ | $CH_2CH_2CH_2NMe_2$ | Me | Me |
| 45 | nBu | N | C | CO | $NC_4H_8$ | $CH_2CH_2CH_2NMe_2$ | Me | Me |
| 46 | nBu | N | C | CO | $NC_5H_{10}$ | $CH_2CH_2CH_2NMe_2$ | Me | Me |
| 47 | nBu | N | C | CO | $NC_4H_8S$ | $CH_2CH_2CH_2NMe_2$ | Me | Me |
| 48 | nBu | N | C | CO | $NC_4H_8NH$ | $CH_2CH_2CH_2NMe_2$ | Me | Me |
| 49 | nBu | N | C | CO | $NC_4H_8NMe$ | $CH_2CH_2CH_2NMe_2$ | Me | Me |
| 50 | nBu | N | C | CO | $NC_4H_8O$ | $CH_2CH_2CH_2NEt_2$ | Me | Me |
| 51 | Et | CH | C | CO | $NC_4H_8O$ | $CH_2CH_2NMe_2$ | Me | Me |
| 52 | nPr | CH | C | CO | $NC_4H_8O$ | $CH_2CH_2NMe_2$ | Me | Me |
| 53 | nPen | CH | C | CO | $NC_4H_8O$ | $CH_2CH_2NMe_2$ | Me | Me |
| 54 | nHex | CH | C | CO | $NC_4H_8O$ | $CH_2CH_2NMe_2$ | Me | Me |
| 55 | nBu | CH | C | CO | $NC_4H_8O$ | $CH_2CH_2NEt_2$ | Me | Me |
| 56 | nBu | CH | C | CO | $NC_4H_8O$ | $CH_2CH_2NMe_2$ | Et | Et |
| 57 | nBu | CH | C | CO | $NC_4H_8$ | $CH_2CH_2NMe_2$ | Me | Me |
| 58 | nBu | CH | C | CO | $NC_5H_{10}$ | $CH_2CH_2NMe_2$ | Me | Me |
| 59 | nBu | CH | C | CO | $NC_4H_8S$ | $CH_2CH_2NMe_2$ | Me | Me |
| 60 | nBu | CH | C | CO | $NC_4H_8NH$ | $CH_2CH_2NMe_2$ | Me | Me |
| 61 | nBu | CH | C | CO | $NC_4H_8NMe$ | $CH_2CH_2NMe_2$ | Me | Me |
| 62 | Et | CH | C | CO | $NC_4H_8NH$ | $CH_2CH_2NMe_2$ | Me | Me |
| 63 | Et | CH | C | CO | $NC_4H_8NMe$ | $CH_2CH_2NMe_2$ | Me | Me |
| 64 | Et | CH | C | CO | $NC_4H_8NnPr$ | $CH_2CH_2NMe_2$ | Me | Me |
| 65 | nPr | CH | C | CO | $NC_4H_8NH$ | $CH_2CH_2NMe_2$ | Me | Me |
| 66 | nPr | CH | C | CO | $NC_4H_8NMe$ | $CH_2CH_2NMe_2$ | Me | Me |
| 67 | nPr | CH | C | CO | $NC_4H_8NnPr$ | $CH_2CH_2NMe_2$ | Me | Me |
| 68 | nHex | CH | C | CO | $NC_4H_8NH$ | $CH_2CH_2NMe_2$ | Me | Me |
| 69 | nHex | CH | C | CO | $NC_4H_8NMe$ | $CH_2CH_2NMe_2$ | Me | Me |
| 70 | nHex | CH | C | CO | $NC_4H_8NnPr$ | $CH_2CH_2NMe_2$ | Me | Me |
| 71 | Et | CH | C | CO | $NC_4H_8O$ | $CH_2CH_2CH_2NMe_2$ | Me | Me |
| 72 | nPr | CH | C | CO | $NC_4H_8O$ | $CH_2CH_2CH_2NMe_2$ | Me | Me |
| 73 | nPen | CH | C | CO | $NC_4H_8O$ | $CH_2CH_2CH_2NMe_2$ | Me | Me |
| 74 | nHex | CH | C | CO | $NC_4H_8O$ | $CH_2CH_2CH_2NMe_2$ | Me | Me |
| 75 | nBu | CH | C | CO | $NC_4H_8$ | $CH_2CH_2CH_2NMe_2$ | Me | Me |
| 76 | nBu | CH | C | CO | $NC_5H_{10}$ | $CH_2CH_2CH_2NMe_2$ | Me | Me |
| 77 | nBu | CH | C | CO | $NC_4H_8S$ | $CH_2CH_2CH_2NMe_2$ | Me | Me |

TABLE 1-continued

| No. | $R^1$ | A | Z | $R^2$ | $R^3$ | $R^4$ | $R^5$ | $R^6$ |
|---|---|---|---|---|---|---|---|---|
| 78 | nBu | CH | C | CO | $NC_4H_8NH$ | $CH_2CH_2CH_2NMe_2$ | Me | Me |
| 79 | nBu | CH | C | CO | $NC_4H_8NMe$ | $CH_2CH_2CH_2NMe_2$ | Me | Me |
| 80 | nBu | CH | C | CO | $NC_4H_8O$ | $CH_2CH_2CH_2NEt_2$ | Me | Me |
| 81 | nBu | N | C | CO | $NC_4H_8NEt$ | H | Me | Me |
| 82 | nPr | N | C | CO | $NC_4H_8NnPr$ | H | Me | Me |
| 83 | nPen | N | C | CO | $NC_4H_8NnPr$ | H | Me | Me |
| 84 | nBu | N | C | CO | $NC_4H_8NnPr$ | H | Et | Et |
| 85 | nBu | N | C | CO | $NC_4H_8NnBu$ | H | Me | Me |
| 86 | nBu | CH | C | CO | $NC_4H_8NEt$ | H | Me | Me |
| 87 | nBu | CH | C | CO | $NC_4H_8NnPr$ | H | Et | Et |

The aromatic compound of the present invention may be prepared by a process known per se. Typical schemes which may be used to prepare the aromatic compound of the present invention are illustrated hereinafter.

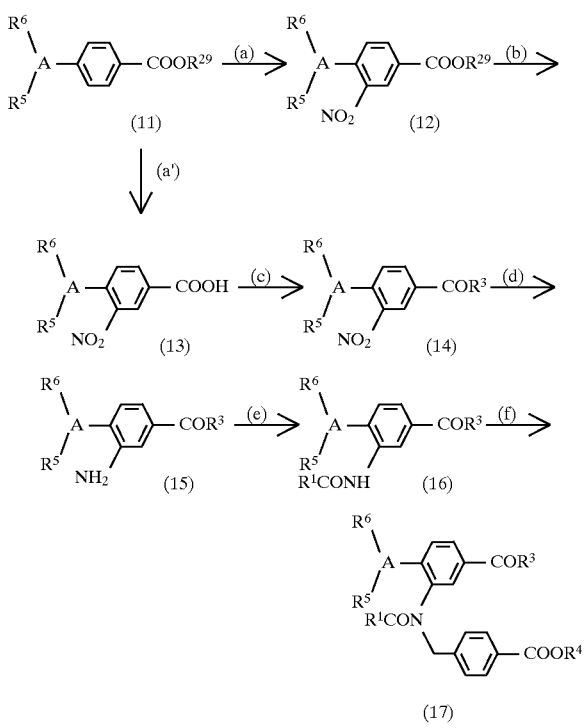

Step [1]-(a), (a')

The compound of the formula (11) wherein $R^5$, $R^6$, and A have the same meanings as above, $R^{29}$ is a hydrogen atom or an alkyl of 1 to 6 carbon atoms, is dissolved in a solvent, such as acetic anhydride, fuming nitric acid is added, and then the reaction is performed at $-10°$ to $30°$ C. for 1 to 10 hours, or a mixed acid of sulfuric and nitric acids is added to the compound of the formula (11), and the reaction is performed in the absence of a solvent at $-10°$ to $30°$ C. for 1 to 10 hours, to obtain the compound of the formula (12) wherein $R^5$, $R^6$, $R^{29}$, and A have the same meanings as above.

Step [1]-(b)

The compound of the formula (12) is dissolved in a solvent, such as methanol, ethanol, tetrahydrofuran, or dioxane. The solution is treated with an alkaline aqueous solution at $10°$ C. to a temperature below the boiling point of the solvent, cooled, and then subjected to an acid precipitation to thereby obtain the compound of the formula (13) wherein $R^5$, $R^6$, and A have the same meanings as above.

Step [1]-(C)

The compound of the formula (13) is dissolved in a solvent, such as chloroform, tetrahydrofuran, benzene, pyridine, or N,N-dimetylformamide, and reacted with a compound capable of converting the —COOH group to a —$COR^3$ group [$R^3$ has the same meaning as above] and an appropriate condensing agent to obtain the compound of the formula (14) wherein $R^5$, $R^6$, $R^3$, and A have the same meanings as above. The compound capable of converting the —COOH group to a —$COR^3$ group is, for example, morpholine when the $R^3$ group is a morpholino group, or may be appropriately selected by those skilled in the art in view of the desired $R^3$ group when the $R^3$ group is a group other than morpholino group.

Step [1]-(d)

The compound of the formula (14) is dissolved in a solvent, such as tetrahydrofuran, alcohol, or ethyl acetate, and treated with an appropriate reducing agent, such as hydrazine monohydrate and 10% palladium/carbon, tin (II) chloride dihydrate, or sodium hydrosulfite, at $0°$ to $100°$ C. to obtain the compound of the formula (15) wherein $R^5$, $R^6$, $R^3$, and A have the same meanings as above.

Step [1]-(e)

The compound of the formula (15) is dissolved in a solvent, such as pyridine or N,N-dimetylformamide, and reacted with a compound having a desired substituent at $-10°$ to $100°$ C. to obtain the compound of the formula (16) wherein $R^5$, $R^6$, $R^3$, $R^1$, and A have the same meanings as above.

Step [1]-(f)

The compound of the formula (16) is dissolved in a solvent, such as dimethyl sulfoxide, N,N-dimethylformamide, tetrahydrofuran, or t-buthyl methyl ether, and reacted with the compound of the formula (18):

$$Y—CH_2(C_6H_4)COOR^4 \quad (18)$$

wherein $R^4$ has the same meaning as above, ($C_6H_4$) is a p-phenylene group, and Y is a leaving group, such as a halogen atom, in the presence of a base, such as sodium hydride or sodium hydroxide at $-20°$ to $100°$ C. to obtain the compound of the formula (17) wherein $R^5$, $R^6$, $R^3$, $R^1$, $R^4$, and A have the same meanings as above. If necessary, one or more protective groups which may exist in the resulting compound can be removed by treating with an acid and/or base.

After the compound wherein $R^4$ is a hydrogen atom is produced by the above treatment, the resulting product may be treated in accordance with a conventional esterification to obtain the compound wherein $R^4$ is a group other than a hydrogen atom.

Scheme (2):

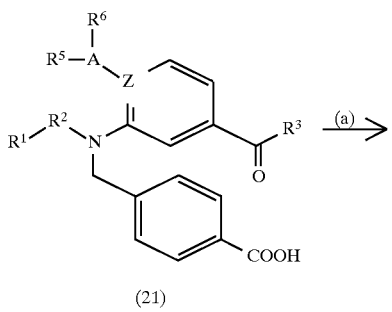

(21)

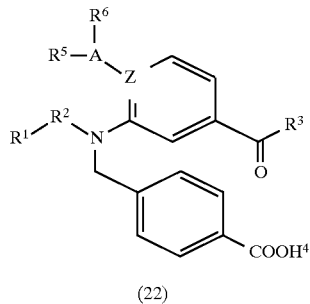

(22)

Step [2]-(a)

The compound of the formula (21) wherein $R^5$, $R^6$, $R^3$, $R^1$, $R^2$, Z, and A have the same meanings as above, is dissolved in an organic solvent, such as chloroform, carbon tetrachloride, toluene, or N,N-dimetylformamide, and if necessary, reacted with an appropriate halogenating agent. Thereafter, the reaction with an appropriate condensing agent and a compound capable of converting the —COOH group to a —COOR$^4$ group wherein $R^4$ has the same meaning as above, is performed in the presence of an appropriate catalyst at –20° to 120° C. for 0.5 to 72 hours to obtain the compound of the formula (22). The appropriate halogenating agent is, for example, thionyl chloride. The appropriate condensing agent is, for example, dicyclohexylcarbodiimide. The appropriate catalyst is, for example, dimethylaminopyridine. The compound capable of converting the —COOH group to a —COOR$^4$ group is, for example, 2-dimethylaminoethanol when the $R^4$ group is a 2-dimethylaminoethyl group, or may be appropriately selected in view of the desired $R^4$ group by those skilled in the art, when the $R^4$ group is a group other than the 2-dimethylaminoethyl group. If necessary, one or more protective groups which may exist in the resulting compound can be removed by treating with an acid and/or base.

The aromatic compound of the formula (I) according to the present invention, or the pharmaceutically acceptable salt thereof, provides a sufficiently effective alleviation of the renal dysfunction without any function to the blood pressure. In addition, the aromatic compound of the formula (I) according to the present invention, or the pharmaceutically acceptable salt thereof, exhibits a superior behavior at a blood concentration. Therefore, the present invention relates to a pharmaceutical composition, particularly an anti-kidney disease agent, containing the aromatic compound of the formula (I), or the pharmaceutically acceptable salt thereof, as an active ingredient.

The aromatic compound of the formula (I) is effective as an agent for treating kidney diseases, such as nephritis, nephropathy, renal failure, nephrotic syndrome, asymptomatic proteinuria, hematuria, diabetic nephropathy, kidney diseases induced by medicine, urinary tract infectious diseases, or prostatitis. The aromatic compound of the formula (I) according to the present invention may be administered to a mammal, including humans, orally or parenterally (such as percutaneously, intravenously or intraperitoneally).

The aromatic compounds of the formula (I) according to the present invention were orally administered to mice at the dose of 500 mg/kg, but no fatalities were observed over a period of one week.

The aromatic compound of the formula (I) may be formulated by adding one or more pharmaceutically acceptable additives to a powder, tablet, granule, capsule, suppository, injection, or oral solution. As the additives, there may be mentioned, for example, magnesium stearate, talc, lactose, dextrin, starches, methylcellulose, fatty acid glycerides, water, propyleneglycol, macrogols, alcohols, crystalline celluloses, hydroxypropylcellulose, low substituted hydroxypropylcellulose, carmelloses, povidone, polyvinylalcohol, or calcium stearate. Further, a coloring agent, stabilizer, antioxidant, preservative, pH adjusting agent, isotonicity, solubilizing agent and/or soothing agent may be contained, if necessary. The granule, tablet, or capsule may be coated with a coating base, such as hydroxypropylmethyl cellulose or hydroxypropylmethyl cellulose phthalate.

The aromatic compound of the formula (I) may be contained at an amount of 0.1 to 500 mg, preferably 1 to 100 mg in a dose unit. The dose of the aromatic compound of the formula (I) is 0.1 to 150 mg/kg body weight, preferably 1 to 100 mg/kg body weight. The dose may be administered once a day, or divided and given twice or 3 times a day. The dose may be appropriately selected with respect to the symptoms of the patient.

It is deemed that one of factors to improve the behavior of the aromatic compound of the formula (I) at a blood concentration is brought about by a water-solubility and moderate fat-solubility due to the acid additive salt formed with the basic nitrogen atom existing in the molecular structure of the aromatic compound of the formula (I) according to the present invention. This asumption, however, does not limit the present invention.

As above, the aromatic compound of the formula (I) according to the present invention, or a salt thereof, provides a sufficient effect on renal dysfunction without affecting the blood pressure. In addition, the aromatic compound of the formula (I) according to the present invention or the pharmaceutically acceptable salt thereof exhibits an improved effect at a blood concentration superior to known aromatic compounds, that is, it provides a superior oral absorption into a body. Therefore, it is possible to effectively and appropriately treat kidney diseases without problems, such as acute renal failure, with the compounds of the present invention, while controlling the blood pressure at a desired level by the use of a suitable antihypertensive drug if necessary.

EXAMPLES

The present invention now will be further illustrated by, but is by no means limited to, the following Examples.

Example 1

Preparation of 4-dimethylamino-3-N-[[[4-(2'-dimethylaminoethoxycarbonyl)phenyl]methyl]valeramido]benzoic acid morpholide ([2]-(22)-1) (Compound No. 1)

Compound No. 184 disclosed in Japanese Unexamined Patent Publication (Kokai) No. 8-48651, i.e., 3-N-[[(4- carboxyphenyl) methyl]valeramido]-4-dimethylaminobenzoic acid morpholide (300 mg) was dissolved in chloroform (6 ml). N,N-Dimetylformamide (catalytic amounts) and thionyl chloride (381 mg) were added to the solution, and the mixture was stirred at room temperature for 2.5 hours. After the reaction was completed, the solvent and an excess amount of thionyl chloride were evaporated, and chloroform (4.5 ml) was added again. Further, 2-dimethylaminoethanol (171 mg) was added, and the mixture was stirred at room temperature for 13 hours. After water was added to the reaction solution, sodium hydrogencarbonate was added to neutralize the solution. The whole was extracted with chloroform. The extract was dried over anhydrous sodium sulfate, and the solvent was evaporated. The residue was purified by silica gel column chromatography (Kieselgel 60=15 g, chloroform/methanol=20/1) to obtain the above-captioned compound ([2]-(22)-1) (Compound No. 1) (288 mg) as a colorless solid.

Melting point: 125.5°–126.5° C.

$^1$H-NMR (500 MHz, CDCl$_3$) δ: 0.85 (t, 3H), 1.24 (sext, 2H), 1.64 (quint, 2H), 2.11 (dt, 1H), 2.26 (dt, 1H), 2.32 (s, 6H), 2.68 (t, 2H), 2.87 (s, 6H), 3.0–3.9 (br, 8H), 4.18 (d, 1H), 4.40 (t, 2H), 5.73 (d, 1H), 6.54 (d, 1H), 7.01 (d, 1H), 7.20 (d, 2H), 7.33 (dd, 1H), 7.87 (d, 2H)

Example 2

Preparation of 4-dimethylamino-3-N-[[[4-(3'-dimethylaminopropoxycarbonyl)phenyl]methyl] valeramido]benzoic acid morpholide ([2]-(22)-2) (Compound No. 2)

Compound No. 184 disclosed in Japanese Unexamined Patent Publication (Kokai) No. 8-48651, i.e., 3-N-[[(4-carboxyphenyl) methyl]valeramido]-4-dimethylaminobenzoic acid morpholide (300 mg) was dissolved in chloroform (6 ml). N,N-Dimetylformamide (catalytic amounts) and thionyl chloride (381 mg) were added, and the mixture was stirred at room temperature for 2 hours. After the reaction was completed, the solvent and an excess amount of thionyl chloride were evaporated, and chloroform (4.5 ml) was added again. Further, 3-dimethylamino-1-propanol (199 mg) was slowly added, and the mixture was stirred at room temperature for 13 hours. After water was added to the reaction mixture, sodium hydrogencarbonate was added to neutralize the solution. The whole was extracted with chloroform. The extract was dried over anhydrous sodium sulfate, and the solvent was evaporated. The residue was purified by silica gel column chromatography (Kieselgel 60=12 g, chloroform/methanol=20/1) to obtain the above-captioned compound ([2]-(22)-2) (Compound No. 2) (313 mg) as a colorless solid.

Melting point: 128.0°–129.0° C.

$^1$H-NMR (500 MHz, CDCl$_3$) δ: 0.85 (t, 3H), 1.24 (sext, 2H), 1.62 (quint, 2H), 1.92 (quint, 2H), 2.11 (dt, 1H), 2.2–2.4 (m, 7H), 2.41 (t, 2H), 2.87 (s, 6H), 3.0–3.9 (br, 8H), 4.17 (d, 1H), 4.34 (t, 2H), 5.73 (d, 1H), 6.54 (d, 1H), 7.01 (d, 1H), 7.22 (d, 2H), 7.33 (dd, 1H), 7.86 (d, 2H)

Example 3

Preparation of 3-N-[[[4-(3'-t-butoxycarbonylamino propoxycarbonyl)phenyl]methyl]valeramido]-4-dimethylamino benzoic acid morpholide ([2]-(22)-3')

Compound No. 184 disclosed in Japanese Unexamined Patent Publication (Kokai) No. 8-48651, i.e., 3-N-[[(4-carboxyphenyl) methyl]valeramido]-4-dimethylaminobenzoic acid morpholide (500 mg) was dissolved in chloroform (10 ml). N,N-Dimetylformamide (catalytic amounts) and thionyl chloride (640 mg) were added to the solution, and the mixture was stirred at room temperature for 2 hours. After the reaction was completed, the solvent and an excess amount of thionyl chloride were evaporated, and pyridine (7.5 ml) was added. Further, 3-t-butoxycarbonylamino-1-propanol (375 mg) was added, and the mixture was stirred at room temperature for 24 hours. Water was added to the reaction mixture. After the whole was extracted with ethyl acetate, the extract was washed with water, and dried over anhydrous sodium sulfate. The solvent was evaporated, and the residue was purified by silica gel column chromatography (Kieselgel 60=27 g, hexane/ethyl acetate=1/1) to obtain the above-captioned compound ([2]-(22)-3') (452 mg) as a colorless solid.

Melting point: 83.0°–85.0° C.

$^1$H-NMR (500 MHz, CDCl$_3$) δ: 0.85 (t, 3H), 1.25 (sext, 2H), 1.44 (s, 9H), 1.62 (quint, 2H), 1.92 (quint, 2H), 2.11 (dt, 1H), 2.28 (dt, 1H), 2.88 (s, 6H), 3.0–3.9 (br, 10H), 4.16 (d, 1H), 4.35 (m, 2H), 4.89 (br s, 1H), 5.75 (d, 1H), 6.51 (d, 1H), 7.01 (d, 1H), 7.23 (d, 2H), 7.33 (dd, 1H), 7.86 (d, 2H)

Example 4

Preparation of 3-N-[[[4-(3'-aminopropoxycarbonyl) phenyl]methyl]valeramido]-4-dimethylaminobenzoic acid morpholide ([2]-(22)-3) (Compound No. 3)

The compound ([2]-(22)-3') (452 mg) prepared in Example 3 was dissolved in tetrahydrofuran (THF) (3.4 ml) and ethanol (3.4 ml). Concentrated hydrochloric acid (2.3 ml) was slowly added while cooling on ice. The mixture was warmed to room temperature, and stirred for 3 hours. After the reaction was completed, the organic solvent was evaporated. Water (10 ml) was added to the residue, and sodium hydrogencarbonate aqueous solution was added to neutralize the solution. The whole was extracted with chloroform. The extract was dried over anhydrous sodium sulfate, and the solvent was evaporated. The residue was purified by silica gel column chromatography to obtain the above-captioned compound ([2]-(22)-3) (Compound No. 3) (225 mg) as colorless crystals.

$^1$H-NMR (500 MHz, CDCl$_3$) δ: 0.85 (t, 3H), 1.25 (sext, 2H), 1.44 (s, 9H), 1.61 (quint, 2H), 1.92 (m, 4H), 2.11 (dt, 1H), 2.28 (dt, 1H), 2.87 (s, 6H), 3.0–3.9 (br, 10H), 4.17 (d, 1H), 5.74 (d, 1H), 6.53 (d, 1H), 7.01 (d, 1H), 7.23 (d, 2H), 7.33 (dd, 1H), 7.86 (d, 2H)

Example 5

Preparation of 3-N-[[[[4-(2'-t-butoxycarbonylamino-2'-ethoxycarbonyl)ethoxycarbonyl]phenyl]methyl] valeramido]-4-dimethylaminobenzoic acid morpholide ([2]-(22) -4')

To a solution of Compound No. 184 disclosed in Japanese Unexamined Patent Publication (Kokai) No. 8-48651, i.e., 3-N-[[(4-carboxyphenyl)methyl]valeramido]-4-dimethylaminobenzoic acid morpholide (3.10 g) in chloroform (62 ml), N,N-dimetylformamide (catalytic amounts) and thionyl chloride (2.4 ml) were added. The mixture was stirred at room temperature for 3 hours, and concentrated. The residue was dissolved in chloroform (31 ml) and triethylamine (1.9 ml), and a solution of t-butoxycarbonyl-L-serine ethyl ester (1.70 g) in chloroform (31 ml) was added. After the mixture was stirred at room temperature for 2 hours, the reaction solution was poured into water. The chloroform layer was washed with saturated brine, dried over anhydrous sodium sulfate, filtered, and concentrated to obtain yellowish brown foam (4.96 g). The crude foam was purified by silica gel column chromatography (Kieselgel 60, n-hexane/ethyl acetate=2/3) to obtain the above-captioned compound ([2]-(22)-4') (2.52 g) as yellow oil.

$^1$H-NMR (500 MHz, CDCl$_3$) δ: 0.85 (t, 3H, J=7.3 Hz), 1.2–1.3 (m, 2H), 1.27 (t, 3H, J=7.3 Hz), 1.45 (s, 9H), 1.6–1.7 (m, 2H), 2.07–2.14 (m, 1H), 2.24–2.8 (m, 1H), 2.88 (s, 6H), 2.9–4.0 (b, 8H), 4.16 (t, 1H, J=13.5 Hz), 4.24 (q, 2H, J=7.3 Hz), 4.60 (b, 2H), 4.67 (b, 1H), 5.56 (dd, 1H, J=7.7, 33.5 Hz), 5.73 (dd, 1H, J=2.5, 14.4 Hz), 6.55 (d, 1H, J=12.8 Hz), 7.02 (d, 1H, J=8.2 Hz), 7.22 (d, 2H, J=8.2 Hz), 7.34 (dd, 1H, J=1.4, 8.2 Hz), 7.83 (dd, 2H, J=1.8, 8.2 Hz)

Example 6

Preparation of 3-N-[[[[4-(2'-amino-2'-ethoxy carbonyl)ethoxycarbonyl]phenyl]methyl] valeramido]-4-dimethyl aminobenzoic acid morpholide ([2]-(22)-4) (Compound No. 4)

To a solution of the compound ([2]-(22)-4') (2.53 g) prepared in Example 5 in a mixture of THF (19 ml) and ethanol (19 ml), concentrated hydrochloric acid (13 ml) was added. The mixture was allowed to stand at room temperature for 3.5 hours. The reaction solution was concentrated, dissolved in chloroform, washed with saturated sodium hydrogencarbonate aqueous solution and saturated brine, dried over anhydrous sodium sulfate, filtered, and concentrated to obtain light yellow foam (2.29 g). The crude foam was purified by silica gel column chromatography (Kieselgel 60, chloroform/methanol=40/1) to obtain the above-captioned compound ([2]-(22)-4) (Compound No. 4) (2.15 g) as colorless foam.

$^1$H-NMR (500 MHz, CDCl$_3$) δ: 0.85 (t, 3H, J=7.3 Hz), 1.18–1.39 (m, 2H), 1.26 (t, 3H, J=7.3 Hz), 1.55–1.75 (m, 4H), 2.07–2.14 (m, 1H), 2.25–2.31 (m, 1H), 2.87 (s, 6H), 3.0–3.8 (b, 8H), 3.82 (t, 1H, J=4.8 Hz), 4.17–4.24 (m, 1H), 4.22 (q, 2H, J=7.3 Hz), 4.5–4.56 (m, 2H), 5.71 (dd, 1H, J=2.3, 14.2 Hz), 6.56 (t, 1H, J=2.3 Hz), 7.01 (d, 1H, J=8.2 Hz), 7.21 (d, 2H, J=7.8 Hz), 7.33 (dd, 1H, J=2.3, 8.2 Hz), 7.85 (d, 1H, J=7.8 Hz)

Example 7

Preparation of 4-dimethylamino-3-N-[[[[4-(1'-t-butoxycarbonyl-2'-ethoxycarbonylpyrrolidin-4'-yloxy)carbonyl]phenyl]methyl]valeramido]benzoic acid morpholide ([2]-(22)-5')

Dicyclohexylcarbodiimide (1.96 g), dimethylaminopyridine (0.29 g), and t-butoxycarbonyl-L-hydroxyproline ethyl ester (1.36 g) were added to a solution of Compound No. 184 disclosed in Japanese Unexamined Patent Publication (Kokai) No. 8-48651, i.e., 3-N-[[(4-carboxyphenyl)methyl]valeramido]-4-dimethylaminobenzoic acid morpholide (2.22 g) in a mixture of pyridine (11 ml) and N,N-dimetylformamide (11 ml). The mixture was stirred at room temperature for 10 days. The reaction solution was concentrated, dissolved in chloroform, washed with distilled water and saturated brine, dried over anhydrous sodium sulfate, filtered, and concentrated to obtain light yellow oil (5.68 g). The crude oil was purified by silica gel column chromatography (LiChroprep Si 60, n-hexane/ethyl acetate= 1/2) to obtain the above-captioned compound ([2]-(22)-5') (1.33 g) as colorless oil.

$^1$H-NMR (500 MHz, CDCl$_3$) δ: 0.85 (t, 3H, J=7.3 Hz), 1.15–1.35 (m, 5H), 1.44, 1.46 (each s, 9H), 1.5–1.7 (m, 2H), 2.1–2.2 (m, 1H), 2.25–2.35 (m, 2H), 2.45–2.55 (m, 1H), 2.88 (s, 6H), 2.95–3.75 (b, 8H), 3.79–3.9 (m, 2H), 4.15–4.3 (m, 3H), 4.35–4.5 (m, 1H), 5.51 (b, 1H), 5.7–5.73 (m, 1H), 6.58 (bs, 1H), 7.02 (d, 1H, J=8.7 Hz), 7.23 (d, 2H, J=8.3 Hz), 7.32–7.35 (m, 1H), 7.85 (d, 2H, J=8.3 Hz)

Example 8

Preparation of 4-dimethylamino-3-N-[[[[4-(2'-ethoxy carbonylpyrrolidin-4'-yloxy)carbonyl] phenyl]methyl]valeramido]benzoic acid morpholide ([2]-(22)-5) (Compound No. 5)

To a solution of the compound ([2]-(22)-5') (1.33 g) in Example 7 in a mixture of THF (10 ml) and ethanol (10 ml), concentrated hydrochloric acid (7 ml) was added. The mixture was allowed to stand at room temperature for 3.5 hours. After the reaction solution was concentrated, the residue was dissolved in chloroform. The solution was washed with saturated sodium hydrogencarbonate aqueous solution and saturated brine, dried over anhydrous sodium sulfate, filtered, and concentrated to obtain colorless oil (1.16 g). The crude oil was purified by silica gel column chromatography (Kieselgel 60, chloroform/methanol=40/1) to obtain the above-captioned compound ([2]-(22)-5) (Compound No. 5) (0.95 g) as colorless oil.

$^1$H-NMR (500 MHz, CDCl$_3$) δ: 0.85 (t, 3H, J=7.3 Hz), 1.2–1.3 (m, 2H), 1.29 (t, 3H, J=7.3 Hz), 1.5–1.85 (m, 3H), 2.07–2.14 (m, 1H), 2.22–2.3 (m, 2H), 2.34–2.39 (m, 1H), 2.88 (s, 6H), 3.0–3.85 (b, 8H), 3.15 (d, 1H, J=17.9 Hz), 3.43 (dd, 1H, J=5.0, 12.4 Hz), 4.01 (t, 1H, J=7.8 Hz), 4.15–4.2 (m, 1H), 4.21 (q, 2H, J=7.3 Hz), 5.47 (b, 1H), 5.74 (d, 1H, J=14.2 Hz), 6.53 (t, 1H, J=1.8 Hz), 7.01 (d, 1H, J=8.3 Hz), 7.21 (d, 2H, J=8.3 Hz), 7.33 (dd, 1H, J=2.3, 8.3 Hz), 7.86 (d, 2H, J=8.3 Hz)

Example 9

Preparation of 3-N-[[[4-(2'-dimethylaminoethoxy carbonyl)phenyl]methyl]valeramido]-4-i-propylbenzoic acid morpholide ([2]-(22)-6) (Compound No. 6)

N,N-Dimetylformamide (catalytic amounts) and thionyl chloride (1.6 ml) were added to a solution of Compound No. 372 disclosed in Japanese Unexamined Patent Publication (Kokai) No. 8-48651, i.e., 3-N-[[(4-carboxyphenyl)methyl] valeramido]-4-i-propylbenzoic acid morpholide (2.01 g) in chloroform (40 ml). The mixture was stirred at room temperature for 3 hours. After the reaction solution was concentrated, the residue was dissolved in chloroform (40 ml) and triethylamine (1.2 ml), and 2-dimethylaminoethanol (0.65 ml) was further added. The mixture was stirred at room temperature for 2 hours, and poured into water. The chloroform layer was washed with saturated brine, dried over anhydrous sodium sulfate, filtered, and concentrated to obtain a yellow solid (2.31 g). The crude solid was purified by silica gel column chromatography (Kieselgel 60, chloroform/methanol=20/1) to obtain the above-captioned compound ([2]-(22)-6) (Compound No. 6) (2.18 g) as a light yellow solid.

Melting point: 106.5°–110° C.

$^1$H-NMR (500 MHz, CDCl$_3$) δ: 0.83 (t, 3H, J=7.3 Hz), 1.18 (d, 3H, J=6.9 Hz), 1.21 (d, 3H, J=6.9 Hz), 1.18–1.25 (m, 2H), 1.54–1.8 (m, 3H), 1.88–1.94 (m, 1H), 1.98–2.04 (m, 1H), 2.33 (s, 6H), 2.70 (t, 2H, J=6.0 Hz), 2.75–3.95 (b,

8H), 3.01–3.07 (m, 1H), 3.99 (d, 1H, J=14.2 Hz), 4.42 (t, 2H, J=6.0 Hz), 5.72 (d, 1H, J=14.2 Hz), 6.59 (d, 1H, J=1.6 Hz), 7.27 (d, 2H, J=8.3 Hz), 7.43 (dd, 1H, J=1.6, 8.0 Hz), 7.46 (d, 1H, J=8.0 Hz), 7.94 (d, 2H, J=8.3 Hz)

Example 10

Preparation of 3-N-[[[4-(3'-dimethylamino-1'-propoxycarbonyl)phenyl]methyl]valeramido]-4-i-propylbenzoic acid morpholide ([2]-(22)-7) (Compound No. 7)

N,N-Dimetylformamide (catalytic amounts) and thionyl chloride (1.6 ml) were added to a solution of Compound No. 372 disclosed in Japanese Unexamined Patent Publication (Kokai) No. 8-48651, i.e., 3-N-[[(4-carboxyphenyl)methyl] valeramido]-4-i-propylbenzoic acid morpholide (2.02 g) in chloroform (40 ml). The mixture was stirred at room temperature for 3 hours. After the reaction solution was concentrated, the residue was dissolved in chloroform (40 ml) and triethylamine (1.2 ml), and 3-dimethylamino-1-propanol (0.76 ml) was further added. The mixture was stirred at room temperature for 2 hours, and poured into water. The chloroform layer was washed with saturated brine, dried over anhydrous sodium sulfate, filtered, and concentrated to obtain a yellow solid (2.52 g). The crude solid was purified silica gel column chromatography (Kieselgel 60, chloroform/methanol=20/1) to obtain the above-captioned compound ([2]-(22)-7) (Compound No. 7) (2.16 g) as a light yellow solid.

Melting point: 95°–98.5° C.

$^1$H-NMR (500 MHz, CDCl$_3$) δ: 0.83 (t, 3H, J=7.3 Hz), 1.18 (d, 3H, J=6.9 Hz), 1.21 (d, 3H, J=6.9 Hz), 1.54–1.7 (m, 4H), 1.88–2.04 (m, 4H), 2.25 (s, 6H), 2.42 (t, 2H, J=6.9 Hz), 2.85–3.9 (b, 8H), 3.04 (quint, 1H, J=6.9 Hz), 3.99 (d, 1H, J=14.2 Hz), 4.37 (t, 2H, J=6.9 Hz), 5.72 (d, 1H, J=14.2 Hz), 6.59 (d, 1H, J=1.4 Hz), 7.27 (d, 2H, J=7.8 Hz), 7.43 (dd, 1H, J=1.4, 7.8 Hz), 7.46 (d, 1H, J=7.8 Hz), 7.92 (d, 2H, J=7.8 Hz)

Example 11

Preparation of 3-N-[[[4-(2'-diethylaminoethoxy carbonyl)phenyl]methyl]valeramido]-4-i-propylbenzoic acid morpholide ([2]-(22)-8) (Compound No. 8)

Compound No. 372 disclosed in Japanese Unexamined Patent Publication (Kokai) No. 8-48651, i.e., 3-N-[[(4-carboxyphenyl) methyl]valeramido]-4-i-propylbenzoic acid morpholide (500 mg) was dissolved in chloroform (7.5 ml). N,N-Dimetylformamide (catalytic amounts) and thionyl chloride (636 mg) were added to the solution, and the mixture was stirred at room temperature for 3 hours. After the reaction was completed, the solvent and an excess amount of thionyl chloride were evaporated, and chloroform (5 ml) was added again. Further, 2-diethylaminoethanol (376 mg) was slowly added, and the mixture was stirred at room temperature overnight. After water was added to the reaction mixture, sodium hydrogencarbonate was added to neutralize the solution, and the whole was extracted with chloroform. The extract was dried over anhydrous sodium sulfate, and the solvent was evaporated. The residue was purified by silica gel column chromatography (Kieselgel 60=50 g, chloroform/methanol=20/1) to obtain the above-captioned compound ([2]-(22)-8) (Compound No. 8) (480 mg) as a colorless solid.

Melting point: 78.0°–82.0° C.

$^1$H-NMR (500 MHz, CDCl$_3$) δ: 0.83 (t, 3H), 1.06 (t, 6H), 1.1–1.3 (m, 8H), 1.58 (quint, 2H), 1.92 (dt, 1H), 2.01 (dt, 1H), 2.62 (q, 4H), 2.84 (t, 2H), 3.04 (sext, 1H), 3.2–3.9 (br, 8H), 4.01 (d, 1H), 4.38 (t, 2H), 5.69 (d, 1H), 6.60 (s, 1H), 7.27 (d, 2H), 7.4–7.5 (m, 2H), 7.92 (d, 2H)

Example 12

Preparation of 3-N-[[[4-(2'-morpholinoethoxy carbonyl)phenyl]methyl]valeramido]-i-propylbenzoic acid morpholide ([2]-(22)-9) (Compound No. 9)

Compound No. 372 disclosed in Japanese Unexamined Patent Publication (Kokai) No. 8-48651, i.e., 3-N-[[(4-carboxyphenyl) methyl]valeramido]-4-i-propylbenzoic acid morpholide (3.00 g) was dissolved in chloroform (60 ml). N,N-Dimetylformamide (catalytic amounts) and thionyl chloride (3.82 g) were added to the solution, and the mixture was stirred at room temperature for 2 hours. After the reaction was completed, the solvent and an excess amount of thionyl chloride were evaporated, and chloroform (45 ml) was added again. Further, 2-morpholinoethanol (2.02 g) was slowly added, and the mixture was stirred at room temperature overnight. After water was added to the reaction mixture, sodium hydrogencarbonate was added to neutralize the solution, and the whole was extracted with chloroform. The extract was dried over anhydrous sodium sulfate, and the solvent was evaporated. The residue was purified by silica gel column chromatography (Kieselgel 60=150 g, chloroform/methanol=50/1) to obtain the above-captioned compound ([2]-(22)-9) (Compound No. 9) (2.98 g) as a colorless solid.

Melting point: 94.5°–98.0° C.

$^1$H-NMR (500 MHz, CDCl$_3$) δ: 0.83 (t, 3H), 1.1–1.3 (m, 2H), 1.59 (quint, 2H), 1.92 (dt, 1H), 2.01 (dt, 1H), 2.56 (t, 4H), 2.76 (t, 2H), 3.04 (sext, 1H), 2.9–3.9 (br, 8H), 3.71 (t, 4H), 3.99 (d, 1H), 4.45 (t, 2H), 5.72 (d, 1H), 6.60 (d, 1H), 7.28 (d, 2H), 7.4–7.5 (m, 2H), 7.92 (d, 2H)

Example 13

Preparation of 4-dimethylamino-3-nitrobenzoic acid 4'-methylpiperazide ([1]-(14)-10)

4-Dimethylamino-3-nitrobenzoic acid ([1]-(13)-10) (12.5 g) was dissolved in N,N-dimetylformamide (375 ml). Hydroxybenzotriazole (10.4 g), triethylamine (10.7 ml), WSCI [1-ethyl-3-(3-dimethylaminopropyl)carbodiimide hydrochloride], and tritylpiperazine (25 g) were added to the solution, and the mixture was stirred at room temperature for 12 hours. After water was added to the reaction solution, the whole was extracted with chloroform. The organic layer was dried over sodium sulfate, and concentrated. The residue was purified by chromatography (Kieselgel 60=500 g, chloroform/methanol=10/1) to obtain the above-captioned compound ([1]-(14)-10) (17.30 g) as reddish brown oil.

$^1$H-NMR (500 MHz, CDCl$_3$) δ: 2.33 (s, 3H), 2.43 (bs, 4H), 2.95 (s, 6H), 3.65 (bs, 4H), 7.01 (d, 1H), 7.50 (dd, 1H), 7.89 (d, 1H)

Example 14

Preparation of 3-amino-4-dimethylaminobenzoic acid 4'-methylpiperazide ([1]-(15)-10)

The compound ([1]-(14)-10) (17.3 g) prepared in Example 13 was dissolved in THF (300 ml) and water (300 ml). Sodium hydrosulfite (51.5 g) was added to the solution, and the mixture was stirred at room temperature for 0.5 hour. To the reaction mixture, potassium carbonate was added to neutralize the solution, and the whole was extracted with chloroform. The organic layer was dried over sodium sulfate, and concentrated. The residue was purified by chromatography (Kieselgel 60=300 g, chloroform/methanol=5/1) to obtain the above-captioned compound ([1]-(15)-10) (10.64 g) as a light yellow solid.

Melting point: 83.1°–84.2° C.

$^1$H-NMR (500 MHz, CDCl$_3$) δ: 2.31 (s, 3H), 2.40 (bs, 4H), 2.66 (s, 3H), 2.67 (s, 3H), 3.40–3.85 (br, 4H), 4.02 (s, 2H), 6.75 (d, 1H), 7.97 (d, 1H), 7.29 (s, 1H)

Example 15

Preparation of 4-dimethylamino-3-valeramidobenzoic acid 4'-methylpiperazide ([1]-(16)-10)

The compound ([1]-(15)-10) (0.32 g) prepared in Example 14 was dissolved in pyridine (3.8 ml). Valeryl chloride (0.16 ml) was added to the solution while cooling on ice, and the mixture was stirred at 0° C. for 1 hour. After water was added to the reaction solution, the whole was extracted with chloroform. The organic layer was dried over sodium sulfate, and concentrated. The residue was purified by column chromatography (Kieselgel 60=15 g, chloroform/methanol=10/1) to obtain the above-captioned compound ([1]-(16)-10) (0.38 g) as yellow oil.

$^1$H-NMR (500 MHz, CDCl$_3$) δ: 0.96 (t, 3H), 1.43 (tq, 2H), 1.73 (tt, 2H), 2.33 (s, 3H), 2.42 (t, 2H), 2.40–2.55 (br, 4H), 2.66 (s, 3H), 3.55 (bs, 2H), 3.78 (bs, 2H), 7.16 (d, 1H), 7.18 (d, 1H), 8.33 (s, 1H), 8.41 (s, 1H)

Example 16

Preparation of 4-dimethylamino-3-[[(4-methoxy carbonylphenyl)methyl]valeramido]benzoic acid 4'-methyl piperazide ([1]-(17)-10')

Dimethyl sulfoxide (3.4 ml) was added to 60% sodium hydride (51.5 mg). To the mixture, a solution of the compound ([1]-(16)-10) (343 mg) prepared in Example 15 in dimethyl sulfoxide (3.4 ml) was added dropwise while cooling on ice. The mixture was stirred at room temperature for 10 minutes. Further, a solution of methyl 4-bromomethylbenzoate (272 mg) in dimethyl sulfoxide (1.7 ml) was added dropwise, and the mixture was stirred at room temperature for 2 hours. Water was added to the reaction solution, and the whole was extracted with chloroform. The organic layer was dried over sodium sulfate, and concentrated. The residue was purified by column chromatography (Kieselgel 60=15 g, chloroform/methanol=10/1) to obtain the above-captioned compound ([1]-(17)-10') (442 mg) as yellow oil.

$^1$H-NMR (500 MHz, CDCl$_3$) δ: 0.85 (t, 3H), 1.25 (tq, 2H), 1.64 (tt, 2H), 2.11 (dt, 1H), 2.25 (s, 3H), 2.29 (dt, 1H), 2.61 (s, 6H), 2.87 (s, 3H), 4.18 (d, 1H), 5.73 (d, 1H), 6.55 (d, 1H), 7.01 (d, 1H), 7.21 (d, 2H), 7.32 (dd, 1H), 7.87 (d, 2H)

Example 17

Preparation of 3-[[(4-carboxyohenyl)methyl]valeramido]-4-dimethylaminobenzoic acid 4'-methylpiperazide ([1]-(17)-10) (Compound No. 10)

The compound ([1]-(17)-10') (0.40 g) prepared in Example 16 was dissolved in methanol (2 ml). To the solution, 1N NaOH aqueous solution (2 ml) was added while cooling on ice. The mixture was stirred at room temperature for 1.5 hours. After 1N HCl aqueous solution was added to neutralize the solution, the reaction solution was concentrated, and dried. The residue was purified by column chromatography (Kieselgel 60=20 g, chloroform/methanol=6/1) to obtain the above-captioned compound ([1]-(17)-10) (Compound No. 10) (169 mg) as a light yellow solid.

Melting point: 115.0°–116.0° C.

$^1$H-NMR (500 MHz, CDCl$_3$) δ: 0.86 (t, 3H), 1.24 (tq, 2H), 1.64 (dd, 5H), 2.08 (dt, 1H), 2.30 (dt, 1H), 2.38 (s, 3H), 2.40–3.70 (br, 8H), 2.92 (s, 6H), 4.08 (d, 1H), 5.88 (d, 1H), 6.35 (s, 1H), 7.02 (d, 1H), 7.14 (bs, 2H), 7.35 (d, 1H), 7.87 (d, 2H)

Example 18

Preparation of 3-amino-4-dimethylaminobenzoic acid 4'-n-propylpiperazide ([1]-(15)-11)

In water (105 ml) and THF (105 ml), 3-nitro-4-dimethyl aminobenzoic acid 4'-n-propylpiperazide ([1]-(14)-11) (5.25 g) was dissolved. Sodium hydrosulfite (16.45 g) was added to the solution, and the reaction solution was stirred at room temperature for 30 minutes. After the reaction was completed, the aqueous layer and the organic layer were separated. The aqueous layer was neutralized with sodium hydrogencarbonate, and extracted with chloroform. The extract and the above organic layer were combined. The mixture was dried over anhydrous sodium sulfate, and the solvent was evaporated. The residue was purified by column chromatography (Kieselgel 60=100 g, chloroform/methanol=20/1) to obtain the above-captioned compound ([1]-(15)-11) (3.39 g) as yellow oil.

$^1$H-NMR (500 MHz, CDCl$_3$) δ: 0.91 (s, 3H), 1.51 (sext, 2H), 2.32 (t, 2H), 2.4–2.6 (br, 4H), 2.67 (s, 6H), 3.4–3.9 (br, 4H), 4.00 (s, 2H), 6.7–6.8 (m, 2H), 6.96 (d, 1H)

Example 19

Preparation of 4-dimethylamino-3-valeramidobenzoic acid 4'-n-propylpiperazide ([1]-(16)-11)

The compound ([1]-(15)-11) (344 mg) prepared in Example 18 was dissolved in pyridine (7 ml). Further, valeryl chloride (201 mg) was added to the solution, and the mixture was stirred at room temperature for 30 minutes. After the reaction was completed, the solvent was evaporated. Sodium hydrogencarbonate aqueous solution was added, and the whole was extracted with chloroform. The extract was dried over anhydrous sodium sulfate, and the solvent was evaporated. The residue was purified by column chromatography (Kieselgel 60=15 g, chloroform/methanol=40/1) to obtain the above-captioned compound ([1]-(16)-11) (358 mg) as light yellow oil.

$^1$H-NMR (500 MHz, CDCl$_3$) δ: 0.91 (t, 3H), 0.96 (t, 3H), 1.44 (sext, 2H), 1.49 (sext, 2H), 1.73 (quint, 2H), 2.33 (t, 2H), 2.43 (t, 2H), 2.50 (br, 4H), 2.66 (s, 3H), 3.52 (br, 2H), 3.77 (br, 2H), 7.1–7.2 (m, 2H), 8.41 (s, 1H), 8.33 (s, 1H)

Example 20

Preparation of 4-dimethylamino-3-N-[[(4-methoxy carbonylphenyl)methyl]valeramido]benzoic acid 4'-n-propyl piperazide ([1]-(17)-11')

The compound ([1]-(16)-11) (344 mg) prepared in Example 19 was dissolved in THF (6 ml). Sodium hydride (38 mg) was added to the solution, and the mixture was stirred at room temperature for 15 minutes. Further, methyl 4-bromomethyl benzoate (199 mg) was added, and the mixture was stirred at room temperature for 1 hour. After the reaction was completed, 1N HCl aqueous solution was added, and the solvent was evaporated. An aqueous solution of sodium hydrogencarbonate was added, and the whole was extracted with chloroform. The extract was dried over sodium sulfate, and the solvent was evaporated. The residue was purified by silica gel column chromatography (Kieselgel 60=20 g, chloroform/methanol=50/1) to obtain the above-captioned compound ([1]-(17)-11') (295 mg) as a light yellow solid.

Melting point: 145.5°–146.5° C.

$^1$H-NMR (500 MHz, CDCl$_3$) δ: 0.85 (t, 3H), 0.91 (t, 3H), 1.24 (sext, 2H), 1.47 (sext, 2H), 1.63 (sext, 2H), 1.9–2.5 (br, 4H), 2.11 (td, 1H), 2.3–2.5 (m, 3H), 2.90 (s, 6H), 2.9–3.9 (br, 4H), 3.88 (s, 3H), 4.18 (d, 1H), 5.73 (d, 1H), 6.54 (d, 1H), 7.01 (d, 1H), 7.21 (d, 2H), 7.34 (dd, 1H), 7.87 (d, 2H)

Example 21

Preparation of 4-dimethylamino-3-N-[[(4-carboxy phenyl)methyl]valeramido]benzoic acid 4'-n-propylpiperazide ([1]-(17)-11) (Compound No. 11)

The compound ([1]-(17)-11') (272 mg) prepared in Example 20 was dissolved in THF (1.4 ml) and methanol (2 ml). To the solution, 1N NaOH aqueous solution (2.7 ml) was added, and the mixture was stirred at room temperature for 2 days. After the reaction was completed, the organic solvent was evaporated. The solution was adjusted to approximately pH 4 with 1N HCl aqueous solution, and the whole was extracted with chloroform. The extract was dried over anhydrous sodium sulfate, and the solvent was evaporated. The residue was purified by silica gel column chromatography (Kieselgel 60=15 g, chloroform/methanol=20/1) to obtain the above-captioned compound ([1]-(17)-11) (Compound No. 11) (187 mg) as a light yellow solid.

Melting point: 113.0°–115.5° C.

$^1$H-NMR (500 MHz, CDCl$_3$) δ: 0.85 (t, 3H), 0.91 (t, 3H), 1.2–1.4 (m, 2H), 1.51 (br, 2H), 1.64 (sext, 2H), 1.9–2.5 (br, 4H), 2.08 (td, 1H), 2.1–4.1 (br, 8H), 2.28 (td, 1H), 2.44 (br, 2H), 2.88 (s, 6H), 3.88 (s, 3H), 4.11 (d, 1H), 5.73 (d, 1H), 6.41 (s, 1H), 6.98 (d, 1H), 7.06 (d, 2H), 7.30 (d, 1H), 7.86 (d, 2H)

Example 22

Preparation of 4-dimethylamino-3-n-heptanamido benzoic acid 4'-n-propylpiperazide ([1]-(16)-12)

The compound ([1]-(15)-11) (380 mg) prepared in Example 18 was dissolved in pyridine (7 ml). Heptanoyl chloride (274 mg) was added to the solution, and the mixture was stirred at room temperature for 30 minutes. After the reaction was completed, the solvent was evaporated. An aqueous solution of sodium hydrogencarbonate was added, and extracted with chloroform. The extract was dried over anhydrous sodium sulfate, and the solvent was evaporated. The residue was purified by column chromatography (Kieselgel 60=15 g, chloroform/methanol=40/1) to obtain the above-captioned compound ([1]-(16)-12) (413 mg) as light yellow oil.

$^1$H-NMR (500 MHz, CDCl$_3$) δ: 0.90 (br, 3H), 0.91 (t, 3H), 1.2–1.4 (m, 6H), 1.51 (sext, 2H), 1.74 (quint, 2H), 2.34 (t, 2H), 2.41 (t, 2H), 2.43 (br, 4H), 2.65 (s, 3H), 3.52 (br, 2H), 3.77 (br, 2H), 7.1–7.2 (m, 2H), 8.33 (s, 1H), 8.41 (s, 1H)

Example 23

Preparation of 4-dimethylamino-3-N-[[(4-methoxy carbonylphenyl)methyl]n-heptanamido]benzoic acid 4'-n-propyl piperazide ([1]-(17)-12')

The compound ([1]-(16)-12) (363 mg) prepared in Example 22 was dissolved in THF (7 ml). Sodium hydride (43 mg) was added to the solution, and the mixture was stirred at room temperature for 15 minutes. Further, methyl 4-bromomethyl benzoate (227 mg) was added to the solution, and the mixture was stirred at room temperature for 2 days. After the reaction was completed, 1N HCl aqueous solution was added, and the solvent was evaporated. An aqueous solution of sodium hydrogencarbonate was added, and the whole was extracted with chloroform. The extract was dried over sodium sulfate, and the solvent was evaporated. The residue was purified by silica gel column chromatography (Kieselgel 60=20 g, chloroform/methanol=70/1) to obtain the above-captioned compound ([1]-(17)-12') (303 mg) as a light yellow solid.

Melting point: 144.5°–145.3° C.

$^1$H-NMR (500 MHz, CDCl$_3$) δ: 0.84 (t, 3H), 0.91 (t, 3H), 1.2–1.3 (m, 6H), 1.47 (sext, 2H), 1.65 (m, 2H), 1.9–2.5 (br, 4H), 2.11 (td, 1H), 2.3–2.5 (m, 3H), 2.87 (s, 6H), 2.9–3.9 (br, 4H), 3.88 (s, 3H), 4.18 (d, 1H), 5.74 (d, 1H), 6.53 (d, 1H), 7.01 (d, 1H), 7.21 (d, 2H), 7.34 (dd, 1H), 7.87 (d, 2H)

Example 24

Preparation of 4-dimethylamino-3-N-[[(4-carboxy phenyl)methyl]n-heptanamido]benzoic acid 4'-n-propyl piperazide ([1]-(17)-12) (Compound No. 12)

The compound ([1]-(17)-12') (285 mg) prepared in Example 23 was dissolved in THF (2 ml) and methanol (4 ml). To the solution, 1N NaOH aqueous solution (3 ml) was added, and the mixture was stirred at room temperature for 2 days. After the reaction was completed, the organic solvent was evaporated. The solution was adjusted to approximately pH 4 with 1N HCl aqueous solution, and the whole was extracted with chloroform. The extract was dried over anhydrous sodium sulfate, and the solvent was evaporated. The residue was purified by silica gel column chromatography (Kieselgel 60=15 g, chloroform/methanol=15/1) to obtain the above-captioned compound ([1]-(17)-12) (Compound No. 12) (196 mg) as a light yellow solid.

Melting point: 78.0°–79.5° C.

$^1$H-NMR (500 MHz, CDCl$_3$) δ: 0.84 (t, 3H), 0.90 (t, 3H), 1.2–1.3 (m, 6H), 1.6–1.8 (m, 4H), 2.11 (td, 1H), 2.3–2.5 (m, 3H), 2.5–3.2 (br, 4H), 2.88 (s, 6H), 3.3–4.1 (br, 4H), 4.12 (d, 1H), 5.86 (d, 1H), 6.40 (s, 1H), 7.01 (d, 1H), 7.13 (d, 2H), 7.34 (dd, 1H), 7.87 (d, 2H)

Example 25

Preparation of 4-dimethylamino-3-n-heptanamido benzoic acid 4'-methylpiperazide ([1]-(16)-13)

In pyridine (12 ml), 3-amino-4-dimethylaminobenzoic acid 4'-methylpiperazide ([1]-(15)-13) (1.00 g) was dissolved. Heptanoyl chloride (0.77 ml) was added to the solution while cooling on ice, and the mixture was stirred at 0° C. for 50 minutes. To the reaction solution, water was added, and the whole was extracted with chloroform. The organic layer was dried over sodium sulfate, and concentrated. The residue was purified by column chromatography (Kieselgel 60=50 g, chloroform/methanol=10/1) to obtain the above-captioned compound ([1]-(16)-13) (1.43 g) as yellow oil.

¹H-NMR (500 MHz, CDCl₃) δ: 0.89 (t, 3H), 1.28–1.45 (m, 6H), 1.74 (tt, 2H), 2.32 (s, 3H), 2.42 (t, 2H), 2.35–2.55 (br, 4H), 2.65 (s, 6H), 3.53 (bs, 2H), 3.76 (bs, 2H), 7.17 (d, 1H), 8.34 (s, 1H), 8.41 (s, 1H)

Example 26

Preparation of 4-dimethylamino-3-[[(4-methoxy carbonylphenyl)methyl]n-heptanamido]benzoic acid 4'-methyl piperazide ([1]-(17)-13')

THF (3 ml) was added to 60% sodium hydride (26.7 mg). To the mixture, a solution of the compound ([1]-(16)-13) (295 mg) prepared in Example 25 in THF (3 ml) was added dropwise. After the mixture was stirred at room temperature for 5 minutes, a solution of methyl 4-bromomethylbenzoate (235 mg) in THF (1.5 ml) was further added dropwise. The mixture was stirred at room temperature for 3 hours. A small amount of water was added to the reaction solution, and the whole was concentrated. The residue was purified by column chromatography (Kieselgel 60=15 g, chloroform/methanol=10/1) to obtain the above-captioned compound ([1]-(17)-13') (254 mg) as a light yellow solid.

Melting point: 120.5°–121.9° C.

¹H-NMR (500 MHz, CDCl₃) δ: 0.84 (t, 3H), 1.14–1.29 (m, 6H), 1.55–1.72 (m, 2H), 2.10 (dt, 1H), 2.25 (s, 3H), 2.29 (dt, 2H), 2.87 (s, 6H), 1.80–2.50 (br, 4H), 2.90–3.80 (br, 4H), 3.88 (s, 3H), 4.18 (d, 1H), 5.74 (d, 1H), 6.54 (d, 1H), 7.01 (d, 1H), 7.21 (d, 2H), 7.33 (dd, 1H), 7.87 (d, 2H)

Example 27

Preparation of 3-[[(4-carboxyohenyl)methyl]n-heptanamido]-4-dimethylaminobenzoic acid 4'-methylpiperazide ([1]-(16)-13) (Compound No. 13)

The compound ([1]-(17)-13') (253 mg) prepared in Example 26 was dissolved in methanol (2.5 ml). To the solution, 1N NaOH aqueous solution (1.25 ml) was added, and the mixture was stirred at room temperature for 30 minutes. After the solution was neutralized with acidic resin CG50, the reaction solution was filtered. The filtrate was concentrated and dried to obtain the above-captioned compound ([1]-(16)-13) (Compound No. 13) (163 mg) as a light yellow solid.

Melting point: 78.0°–79.4° C.

¹H-NMR (500 MHz, CDCl₃) δ: 0.85 (t, 3H), 1.16–1.30 (m, 6H), 1.55–1.74 (m, 2H), 2.09 (ddd, 1H), 2.29 (ddd, 2H), 2.40 (s, 3H), 2.45 (bs, 2H), 2.92 (s, 6H), 2.55–3.00 (br, 6H), 4.10 (d, 1H), 5.92 (d, 1H), 6.36 (d, 1H), 7.03 (d, 1H), 7.18 (d, 2H), 7.38 (dd, 1H), 7.89 (d, 2H)

Example 28

Preparation of 4-dimethylamino-3-n-octanamido benzoic acid 4'-methylpiperazide ([1]-(16)-14)

In pyridine (12 ml), 3-amino-4-dimethylaminobenzoic acid 4'-methylpiperazide ([1]-(15)-14) (1.02 g) was dissolved. Octanoyl chloride (0.9 ml) was added to the solution while cooling on ice, and the mixture was stirred at 0° C. for 2 hours. Water was added to the reaction solution, and the whole was extracted with chloroform. The organic layer was dried over sodium sulfate, and concentrated. The residue was purified by column chromatography (Kieselgel 60=40 g, chloroform/methanol=10/1) to obtain the above-captioned compound ([1]-(16)-14) (1.47 g) as yellow oil.

¹H-NMR (500 MHz, CDCl₃) δ: 0.89 (t, 3H), 1.19–1.42 (m, 8H), 1.74 (tt, 2H), 2.32 (s, 3H), 2.41 (t, 2H), 2.35–2.55 (br, 4H), 2.66 (s, 6H), 3.54 (bs, 2H), 3.77 (bs, 2H), 7.16 (d, 1H), 7.18 (d, 1H), 8.33 (s, 1H), 8.41 (s, 1H)

Example 29

Preparation of 3-[[(4-carboxyphenyl)methyl]n-octanamido]-4-dimethylaminobenzoic acid 4'-methylpiperazide ([1]-(17)-14) (Compound No. 14)

THF (15 ml) was added to 60% sodium hydride (0.2 g). To the mixture, a solution of the compound ([1]-(16)-14) (1.47 g) prepared in Example 28 in THF (15 ml) was added dropwise. After the mixture was stirred at room temperature for 10 minutes, a solution of methyl 4-bromomethylbenzoate (1.13 g) in THF (7.5 ml) was added dropwise. The mixture was stirred at room temperature for 2 hours. Water was added to the reaction solution, and the whole was extracted with chloroform. The organic layer was dried over sodium sulfate, concentrated, and purified by column chromatography (Kieselgel 60=20 g, chloroform/methanol=20/1) to obtain a crude product containing the compound ([1]-(17)-14') (911 mg). The crude product (900 mg) was dissolved in methanol (9 ml) and THF (9 ml). To the solution, 1N NaOH aqueous solution (9 ml) was added, and the mixture was stirred at room temperature for 3.5 hours. The mixture was neutralized with 1N HCl aqueous solution, and extracted with chloroform. The organic layer was dried over sodium sulfate, and concentrated. The residue was purified by column chromatography (Kieselgel 60=20 g, chloroform/methanol=5/1) to obtain the above-captioned compound ([1]-(17)-14) (Compound No. 14) (308 mg) as a light yellow solid.

Melting point: 91.5°–93.0° C.

¹H-NMR (500 MHz, CDCl₃) δ: 0.85 (t, 3H), 1.15–1.32 (m, 8H), 1.55–1.73 (m, 2H), 2.07 (ddd, 1H), 2.28 (ddd, 1H), 2.37 (s, 3H), 2.43 (bs, 2H), 2.55–3.00 (br, 6H), 2.91 (s, 6H), 4.09 (d, 1H), 5.90 (d, 1H), 6.35 (s, 2H), 7.02 (d, 1H), 7.16 (d, 2H), 7.36 (d, 1H), 7.88 (d, 2H)

Example 30

Preparation of 3-nitro-4-i-propylbenzoic acid 4'-methylpiperazide ([1]-(14)-15)

In dimetylformamide (145 ml), 3-nitro-4-i-propylbenzoic acid ([1]-(13)-15) (9.7 g) was dissolved. To the solution, hydroxybenzotriazole (8.1 g), triethylamine (8.3 ml), WSCI (11.5 g), and methylpiperazine (6.7 ml) were added, and the mixture was stirred at room temperature for 15 hours. Water was added to the reaction solution, and the whole was extracted with chloroform. The organic layer was dried over sodium sulfate, and concentrated. The residue was purified by column chromatography (Kieselgel 60=200 g, chloroform/methanol=15/1) to obtain the above-captioned compound ([1]-(14)-15) (13.5 g) as yellow oil.

¹H-NMR (500 MHz, CDCl₃) δ: 1.31 (d, 6H), 2.33 (s, 3H), 2.39 (bs, 2H), 2.48 (bs, 2H), 3.44 (sept, 1H), 3.45 (bs, 2H), 3.79 (bs, 2H), 7.54 (d, 1H), 7.59 (dd, 1H), 7.75 (d, 1H)

Example 31

Preparation of 3-amino-4-i-propylbenzoic acid 4'-methylpiperazide ([1]-(15)-15)

The compound ([1]-(14)-15) (13.5 g) prepared in Example 30 was dissolved in ethanol (650 ml). To the solution, 10% Pd—C (1.35 g) and hydrazine monohydrate (13.5 ml) were added. The mixture was stirred at 65° C. for 24 hours. After the reaction solution was filtered, the filtrate was concentrated and dried. The residue was purified by column chromatography (Kieselgel 60=240 g, chloroform/methanol=10/1) to obtain the above-captioned compound ([1]-(15)-15) (12.0 g) as light reddish brown oil.

$^1$H-NMR (500 MHz, CDCl$_3$) δ: 1.25 (d, 6H), 2.31 (s, 3H), 2.30–2.55 (br, 4H), 3.40–3.85 (br, 6H), 6.71 (d, 1H), 6.76 (dd, 1H), 7.13 (d, 1H)

Example 32

Preparation of 4-i-propyl-3-valeramidobenzoic acid 4'-methylpiperazide ([1]-(16)-15)

The compound ([1]-(15)-15) (11.69 g) prepared in Example 31 was dissolved in pyridine (2.6 ml). To the solution, valeryl chloride (0.1 ml) was added while cooling on ice. The mixture was stirred at 0° C. for 1.5 hours. After water was added to the reaction solution, the whole was extracted with chloroform. The organic layer was dried over sodium sulfate, and concentrated. The residue was purified by column chromatography (Kieselgel 60=15 g, chloroform/methanol=10/1) to obtain the above-captioned compound ([1]-(16)-15) (115.9 mg) as yellow oil.

$^1$H-NMR (500 MHz, CDCl$_3$) δ: 0.92 (t, 3H), 1.24 (d, 6H), 1.44 (tq, 2H), 1.73 (tt, 2H), 2.33 (s, 3H), 2.40 (t, 2H), 2.30–2.55 (br, 4H), 3.02 (sept, 1H), 3.56 (bs, 2H), 3.80 (bs, 2H), 7.17 (d, 1H), 7.25 (d, 1H), 7.45 (s, 1H), 7.74 (bs, 1H)

Example 33

Preparation of 3-[[4-(methoxycarbonylphenyl)methyl]valeramido]-4-i-propylbenzoic acid 4'-methylpiperazide ([1]-(17)-15')

Dimethyl sulfoxide (3 ml) was added to 60% sodium hydride (26.7 mg). To the mixture, a solution of the compound ([1]-(16)-15) (295 mg) prepared in Example 32 in dimethyl sulfoxide (3 ml) was added dropwise. The whole was stirred at room temperature for 5 minutes. A solution of methyl 4-bromomethyl benzoate (235 mg) in dimethyl sulfoxide (1.5 ml) was further added dropwise, and the whole was stirred at room temperature for 3 hours. To the reaction solution, a small amount of water was added, and the whole was concentrated. The residue was purified by column chromatography (Kieselgel 60=15 g, chloroform/methanol=10/1) to obtain the above-captioned compound ([1]-(17)-15') (254 mg) as light yellow foam.

$^1$H-NMR (500 MHz, CDCl$_3$) δ: 0.86 (t, 3H), 1.10 (d, 6H), 1.30 (tq, 2H), 1.57 (tt, 2H), 2.35 (bs, 2H), 2.80–3.35 (br, 4H), 3.09 (sept, 1H), 3.19 (s, 3H), 3.90 (s, 3H), 3.75–4.10 (br, 4H), 5.01 (bs, 2H), 7.23 (d, 1H), 7.44 (bd, 1H), 7.56 (bs, 1H), 7.67 (d, 2H), 7.95 (d, 2H)

Example 34

Preparation of 3-[[(4-carboxyphenyl)methyl]valeramido]-4-i-propylbenzoic acid 4'-methylpiperazide ([1]-(17)-15) (Compound No. 15)

The compound ([1]-(17)-15') (253 mg) prepared in Example 33 was dissolved in methanol (2.5 ml). To the solution, 1N NaOH aqueous solution (1.25 ml) was added, and the mixture was stirred at room temperature for 30 minutes. After the solution was neutralized with acidic resin CG50, the reaction solution was filtered. The filtrate was concentrated and dried to obtain the above-captioned compound ([1]-(17)-15) (Compound No. 15) (163 mg) as a light yellow solid.

$^1$H-NMR (500 MHz, CDCl$_3$) δ: 0.99 (t, 3H), 1.23 (d, 6H), 1.45 (tq, 2H), 1.72 (tt, 2H), 2.46 (t, 2H), 3.14 (s, 3H), 3.22 (sept, 1H), 3.31 (s, 2H), 3.48 (bs, 2H), 3.65 (bt, 2H), 3.86 (bt, 2H), 4.73 (s, 2H), 7.40 (dd, 1H), 7.44 (d, 1H), 7.49 (d, 1H), 7.59 (d, 2H), 8.05 (d, 2H)

Example 35

Preparation of 3-[[(4-ethoxycarbonylphenyl)methyl]valeramido]-4-i-propylbenzoic acid 4'-methylpiperazide ([1]-(17)-16) (Compound No. 16)

In carbon tetrachloride (3.5 ml), 3-[[(4-carboxyphenyl)methyl]valeramido]-4-i-propylbenzoic acid 4'-methylpiperazide ([1]-(17)-15) (Compound No. 15) (363 mg) was dissolved. To the solution, dimetylformamide (36 μl) and thionyl chloride (0.55 ml) were added, and the mixture was stirred at 60° C. for 20 minutes. The reaction solution was concentrated and dried. The residue was dissolved in chloroform (5 ml). Triethylamine (0.1 ml) and ethanol (0.1 ml) were added to the solution, and the mixture was stirred at room temperature for 2 hours. To the reaction solution, saturated sodium hydrogencarbonate aqueous solution (5 ml) was added, and the whole was extracted with chloroform. The organic layer was dried over sodium sulfate, and concentrated. The residue was purified by column chromatography (LiChroprep Si 60=30 g, chloroform/methanol=5/1) to obtain the above-captioned compound ([1]-(17)-16) (Compound No. 16) (200 mg) as a light yellow solid.

Melting point: 153.2°–155.5° C.

$^1$H-NMR (500 MHz, CDCl$_3$) δ: 0.82 (t, 3H), 1.15–1.28 (m, 8H), 1.33 (t, 3H), 1.58 (tt, 2H), 1.89 (dt, 1H), 1.99 (dt, 1H), 3.05 (sept, 1H), 3.34 (s, 3H), 3.40–3.65 (br, 2H), 3.77–3.97 (br, 4H), 4.19–4.30 (br, 2H), 5.36 (bd, 1H), 5.82 (bd, 1H), 6.52 (bs, 1H), 7.48 (d, 1H), 7.59 (d, 1H), 7.77 (d, 2H), 8.10 (d, 2H)

Example 36

Preparation of 4-i-propyl-3-nitrobenzoic acid N-[2-(diethylamino)ethyl]-N-ethylamide ([1]-(14)-17)

In chloroform (5.0 ml), 3-nitro-4-i-propylbenzoic acid ([1]-(13)-17) (500 mg) was dissolved. Dimetylformamide (50 μl) and thionyl chloride (1.74 ml) were added to the solution. The mixture was stirred at 65° C. for 45 minutes. The reaction solution was concentrated and dried. The residue was dissolved in chloroform (7.5 ml). Further, triethylamine (1.0 ml) and N,N,N'-triethylethylenediamine (0.6 ml) were added, and the mixture was stirred at room temperature for 18 hours. To the reaction solution, saturated sodium hydrogencarbonate aqueous solution (5 ml) was added, and the whole was extracted with chloroform. The organic layer was dried over sodium sulfate, and concentrated. The residue was purified by column chromatography (LiChroprep Si 60=20 g, hexane/acetone=1/4) to obtain the above-captioned compound ([1]-(14)-17) (590 mg) as yellow oil.

$^1$H-NMR (500 MHz, CDCl$_3$) δ: 0.70–1.30 (br, 9H), 1.30 (d, 6H), 2.20–2.75 (br, 6H), 3.15–3.65 (br, 4H), 3.43 (sept, 1H), 7.51 (d, 1H), 7.57 (bs, 1H), 7.74 (bs, 1H)

Example 37

Preparation of 3-amino-4-i-propylbenzoic acid N-[2-(diethylamino)ethyl]-N-ethylamide ([1]-(15)-17)

The compound ([1]-(14)-17) (573 mg) prepared in Example 36 was dissolved in ethanol (28.6 ml). To the solution, 10% Pd—C (57 mg) and hydrazine monohydrate (0.60 ml) were added, and the mixture was stirred at 65° C. for 1 hour. The reaction solution was filtered. The filtrate was concentrated and dried. The residue was purified by column chromatography (LiChroprep Si 60=20 g, hexane/acetone=1/5) to obtain the above-captioned compound ([1]-(15)-17) (522 mg) as colorless oil.

$^1$H-NMR (500 MHz, CDCl$_3$) δ: 0.75–1.30 (br, 9H), 1.24 (d, 6H), 2.20–2.75 (br, 6H), 2.89 (sept, 1H), 3.20–3.60 (br, 4H), 3.70 (bs, 2H), 6.67 (d, 1H), 6.74 (dd, 1H), 7.11 (d, 1H)

Example 38

Preparation of 4-i-propyl-3-valeramidobenzoic acid N-[2-(diethylamino)ethyl]-N-ethylamide ([1]-(16)-17)

The compound ([1]-(15)-17) (504 mg) prepared in Example 37 was dissolved in pyridine (6.0 ml). Valeryl chloride (0.24 ml) was added to the solution while cooling on ice, and the mixture was stirred at 0° C. for 1 hour. To the reaction solution, saturated sodium hydrogencarbonate aqueous solution (10 ml) was added, and the whole was extracted with chloroform. The organic layer was dried over sodium sulfate, and concentrated. The residue was purified by column chromatography (LiChroprep Si 60=20 g, hexane/acetone=1/4) to obtain the above-captioned compound ([1]-(16)-17) (423 mg) as yellow oil.

$^1$H-NMR (500 MHz, CDCl$_3$) δ: 0.75–1.28 (br, 13H), 1.21 (d, 6H), 1.35–1.47 (br, 2H), 1.65–1.80 (br, 2H), 2.37–2.75 (br, 7H), 2.98–3.05 (br, 1H), 3.25–3.38 (br, 2H), 3.49–3.60 (br, 2H), 7.14 (bs, 1H), 7.24 (d, 1H), 7.48–7.63 (br, 2H)

Example 39

Preparation of 3-[[(4-methoxycarbonylphenyl)methyl]valeramido]-4-i-propylbenzoic acid N-ethyl-N-[2-(diethylamino)ethyl]amide ([1]-(17)-17')

THF (4 ml) was added to 60% NaH (54 mg). A solution of the compound ([1]-(16)-17) (407 mg) prepared in Example 38 in tetrahydrofuran (4 ml) was added dropwise while cooling on ice. After the mixture was stirred at room temperature for 15 minutes, a solution of methyl 4-bromomethylbenzoate (287 mg) in THF (2 ml) was added dropwise while cooling on ice. The mixture was stirred at 0° C. for 1.5 hours. To the reaction solution, water was added, and the whole was extracted with ethyl acetate. The organic layer was dried over sodium sulfate, and concentrated. The residue was purified by column chromatography (LiChroprep Si 60=20 g, hexane/acetone=1/1) to obtain the above-captioned compound ([1]-(17)-17') (290.3 mg) as colorless syrup.

$^1$H-NMR (500 MHz, CDCl$_3$) δ: 0.83 (t, 3H), 0.80–1.28 (br, 11H), 1.59 (tt, 2H), 1.94 (dt, 1H), 2.03 (dt, 1H), 2.21–2.38 (br, 2H), 2.45–2.66 (br, 4H), 2.90–3.10 (br, 3H), 3.33–3.60 (br, 2H), 3.90 (s, 3H), 4.13 (bd, 1H), 5.57 (bd, 1H), 6.67 (bs, 1H), 7.29 (d, 2H), 7.37 (d, 1H), 7.41 (d, 1H), 7.93 (d, 2H)

Example 40

Preparation of 3-[[(4-carboxyphenyl)methyl]valeramido-4-i-propylbenzoic acid N-[2-(diethylamino)ethyl]-N-ethylamide ([1]-(17)-17) (Compound No. 17)

The compound ([1]-(17)-17') (275 mg) prepared in Example 39 was dissolved in methanol (2.7 ml). To the solution, 1N NaOH aqueous solution (2.7 ml) was added while cooling on ice. The mixture was stirred at room temperature for 2 hours. The reaction solution was neutralized with 1N HCl aqueous solution, and the whole was extracted with chloroform. The organic layer was dried over sodium sulfate, concentrated, and dried to obtain the above-captioned compound ([1]-(17)-17) (Compound No. 17) (262 mg) as a colorless solid.

Melting point: 67.0°–67.8° C.

$^1$H-NMR (500 MHz, CDCl$_3$) δ: 0.75 (t, 3H), 0.83 (t, 3H), 1.19–1.30 (m, 11H), 1.34 (d, 3H), 1.60 (tt, 2H), 1.90 (dt, 1H), 2.03 (dt, 1H), 2.81–2.94 (br, 2H), 2.94–3.18 (br, 6H), 3.64 (d, 1H), 3.60–3.80 (br, 2H), 6.06 (d, 1H), 6.39 (s, 1H), 7.12 (d, 2H), 7.33 (d, 1H), 7.45 (d, 1H), 7.88 (d, 2H)

Example 41

Preparation of 3-n-heptanamido-4-i-propylbenzoic acid 4'-methylpiperazide ([1]-(16)-18)

To a solution of 3-amino-4-isopropylbenzoic acid 4'-methylpiperazide ([1]-(15)-18) (0.52 g) in pyridine (6.3 ml), enanthyl chloride (0.31 ml) was added dropwise under stirring while cooling on ice. After the mixture was stirred for 1.5 hours while cooling on ice, the reaction solution was concentrated. The resulting yellow foam (0.97 g) was purified by silica gel column chromatography (Kieselgel 60, chloroform/methanol=15/1) to obtain the above-captioned compound ([1]-(16)-18) (0.58 g) as yellowish brown foam.

$^1$H-NMR (500 MHz, CDCl$_3$) δ: 0.90 (t, 3H, J=6.4 Hz), 1.23 (d, 6H, J=6.9 Hz), 1.33 (bs, 4H), 1.41 (bs, 2H), 1.55–1.8 (b, 4H), 2.3–2.55 (m, 5H), 2.31 (s, 3H), 3.02 (bt, 1H, J=6.4 Hz), 3.53 (bs, 2H), 3.78 (bs, 2H), 7.15–7.35 (m, 2H), 7.64 (b, 1H)

Example 42

Preparation of 3-N-[[(4-methoxycarbonylphenyl)methyl]n-heptanamido]4-i-propylbenzoic acid N-methyl piperazide ([1]-(17)-18')

Oily part of 60% sodium hydride (0.042 g) was washed with n-hexane, and suspended in THF (3.0 ml). To the suspension, a solution of the compound ([1]-(16)-18) (0.30 g) prepared in Example 41 in THF (3.0 ml) was added dropwise under stirring while cooling on ice. At the same temperature, a solution of methyl 4-bromomethylbenzoate (0.22 g) in THF (1.5 ml) was then added dropwise, and the mixture was stirred for 0.5 hour. After the mixture was further stirred at room temperature for 2 hours, the reaction solution was poured into water, and the whole was extracted with ethyl acetate. The ethyl acetate layer was washed with distilled water and saturated brine, dried over anhydrous sodium sulfate, filtered, and concentrated to obtain yellowish orange oil (0.50 g). The crude oil was purified by silica gel column chromatography (Kieselgel 60, chloroform/methanol=20/1) to obtain the above-captioned compound ([1]-(17)-18') (0.30 g) as a light yellow solid.

Melting point: 138°–139.5° C.

$^1$H-NMR (500 MHz, CDCl$_3$) δ: 0.84 (t, 3H, J=7.3 Hz), 1.15–1.35 (m, 6H), 1.19, 1.21 (each d, each 3H, J=6.9 Hz), 1.55–1.65 (m, 2H), 1.7–3.8 (b, 8H), 1.9–2.05 (m, 2H), 2.25 (s, 3H), 2.95–3.1 (m, 1H), 3.90 (s, 3H), 3.98 (d, 1H, J=14.2 Hz), 5.73 (d, 1H, J=14.2 Hz), 6.59 (d, 1H, J=1.4 Hz), 7.28 (d, 2H, J=8.3 Hz), 7.42 (dd, 1H, J=1.4, 8.3 Hz), 7.45 (d, 1H, J=8.3 Hz)

Example 43

Preparation of 3-N-[[(4-carboxyphenyl)methyl]n-heptanamido]-4-i-propylbenzoic acid 4'-methylpiperazide ([1]-(17)-18) (Compound No. 18)

To a solution of the compound ([1]-(17)-18') (0.27 g) prepared in Example 42 in methanol (1.1 ml) and THF (1.1 ml), 1N NaOH aqueous solution (2.1 ml) was added, and the mixture was allowed to stand at room temperature for 0.5 hour. The reaction solution was neutralized with HCl, and concentrated to obtain light yellow foam (0.27 g). The crude foam was purified by silica gel column chromatography (Kieselgel 60, chloroform/methanol=5/1) to obtain the above-captioned compound ([1]-(17)-18) (Compound No. 18) (0.26 g) as a light yellow solid.

Melting point: 102.5°–106° C.

$^1$H-NMR (500 MHz, CDCl$_3$) δ: 0.84 (t, 3H, J=7.3 Hz), 1.0–1.4 (m, 6H), 1.23, 1.36 (each d, each 3H, J=6.9 Hz), 1.4–1.7 (m, 2H), 1.8–1.9 (m, 1H), 1.9–2.1 (m, 1H), 2.2–5.0 (b, 8H), 2.37 (s, 3H), 3.0–3.2 (m, 1H), 3.65 (d, 1H, J=14.2 Hz), 6.14 (d, 1H, J=14.2 Hz), 6.38 (s, 1H), 7.21 (d, 2H, J=7.8 Hz), 7.51 (s, 2H), 7.96 (d, 2H, J=7.8 Hz)

Example 44

Preparation of 3-nitro-4-i-propylbenzoic acid 4'-n-propylpiperazide ([1]-(14)-19)

In chloroform (5.0 ml), 3-nitro-4-i-propylbenzoic acid ([1]-(13)-19) (500 mg) was dissolved. To the solution, dimetylformamide (50 μl) and thionyl chloride (1.74 ml) were added, and the mixture was stirred at 60° C. for 45 minutes. The reaction solution was concentrated and dried. The residue was dissolved in chloroform (7.5 ml). To the solution, triethylamine (1.0 ml) and n-propylpiperazine dihydrochloride (0.6 g) were added, and the mixture was stirred at room temperature for 4 hours. To the reaction solution, saturated sodium hydrogencarbonate aqueous solution (5 ml) was added, and the whole was extracted with chloroform. The organic layer was dried over sodium sulfate, and concentrated. The residue was purified by column chromatography (LiChroprep Si 60=25 g, hexane/acetone=1/4) to obtain the above-captioned compound ([1]-(14)-19) (761 mg) as yellow oil.

$^1$H-NMR (500 MHz, CDCl$_3$) δ: 0.92 (t, 3H), 1.31 (d, 6H), 1.51 (tq, 2H), 2.35 (t, 2H), 2.41 (bs, 2H), 2.51 (bs, 2H), 3.43 (sept, 1H), 3.45 (bs, 2H), 3.79 (bs, 2H), 7.53 (d, 1H), 7.59 (dd, 1H), 7.75 (d, 1H)

Example 45

Preparation of 4-i-propyl-3-valeramidobenzoic acid 4'-n-propylpiperazide ([1]-(16)-19)

The compound ([1]-(14)-19) (231 mg) prepared in Example 44 was dissolved in ethanol (11.6 ml). To the solution, 10% Pd—C (23 mg) and hydrazine monohydrate (0.23 ml) were added, and the mixture was stirred at 70° C. for 1 hour. The reaction solution was filtered, and the filtrate was concentrated and dried to obtain the residue (205.6 mg). A part (186.6 mg) of the residue was dissolved in pyridine (2.2 ml). After valeryl chloride (0.12 ml) was added to the solution while cooling on ice, the mixture was stirred at 0° C. for 1 hour. To the reaction solution, saturated sodium hydrogencarbonate aqueous solution (5 ml) was added, and the whole was extracted with chloroform. The organic layer was dried over sodium sulfate, and concentrated. The residue was purified by column chromatography (LiChroprep Si 60=25 g, hexane/acetone=1/4) to obtain the above-captioned compound ([1]-(16)-19) (288 mg) as yellow oil.

$^1$H-NMR (500 MHz, CDCl$_3$) δ: 0.90 (t, 3H), 0.97 (t, 3H), 1.23 (d, 6H), 1.43 (tq, 2H), 1.50 (tq, 2H), 1.74 (tt, 2H), 2.33 (t, 2H), 2.35–2.45 (br, 4H), 2.50 (bs, 2H), 3.02 (sept, 1H), 3.52 (bs, 2H), 3.77 (bs, 2H), 7.21 (d, 1H), 7.28 (d, 1H), 7.60 (s, 1H)

Example 46

Preparation of 3-[[(4-methoxycarbonylphenyl)methyl]valeramido]-4-i-propylbenzoic acid 4'-n-propyl piperazide ([1]-(17)-19')

THF (93 ml) was added to 60% NaH (1.3 g). To the mixture, a solution of the compound ([1]-(16)-19) (9.255 g) prepared in Example 45 in THF (46 ml) was added dropwise while cooling on ice. After the whole was stirred at room temperature for 15 minutes, a solution of methyl 4-bromomethyl benzoate (7.4 g) in THF (46 ml) was further added dropwise while cooling on ice. The whole was stirred at room temperature for 1 hour, and water (500 ml) was added to the reaction solution. The whole was extracted with chloroform. The organic layer was dried over sodium sulfate, and concentrated. The residue was purified by column chromatography (LiChroprep Si 60=400 g, hexane/acetone=1/1) to obtain the above-captioned compound ([1]-(17)-19') (9.439 g) as a yellowish white solid.

$^1$H-NMR (500 MHz, CDCl$_3$) δ: 0.83 (t, 3H), 0.92 (t, 3H), 1.15–1.25 (m, 8H), 1.48 (tq, 2H), 1.60 (tt, 2H), 1.63 (bs, 2H), 1.97 (ddt, 2H), 2.26 (bt, 2H), 2.30–2.55 (br, 4H), 3.01 (bs, 2H), 3.04 (sept, 1H), 3.67 (bs, 2H), 3.99 (d, 1H), 5.72 (d, 2H), 6.59 (d, 1H), 7.28 (d, 2H), 7.42 (dd, 1H), 7.45 (d, 1H), 7.93 (d, 2H)

Example 47

Preparation of 3-[[(4-carboxyphenyl)methyl]valeramido]-4-i-propylbenzoic acid 4'-n-propylpiperazide ([1]-(17)-19) (Compound No. 19)

The compound ([1]-(17)-19') (9.439 g) prepared in Example 46 was dissolved in methanol (94 ml) and THF (94 ml). To the solution, 1N NaOH aqueous solution (94 ml) was added while cooling on ice, and the mixture was stirred at room temperature for 3 hours. The reaction solution was neutralized with 1N HCl aqueous solution, and the whole was concentrated and dried. The residue was purified by column chromatography (LiChroprep Si 60=150 g, chloroform/methanol=10/1) to obtain the above-captioned compound ([1]-(17)-19) (Compound No. 19) (8.228 g) as a colorless solid.

Melting point: 157.8°–158.7° C.

$^1$H-NMR (500 MHz, CDCl$_3$) δ: 0.84 (t, 3H), 0.89 (t, 3H), 1.15–1.25 (m, 5H), 1.33 (d, 3H), 1.52–1.67 (m, 4H), 1.89 (dt, 1H), 2.03 (dt, 1H), 2.15 (bs, 1H), 2.40–2.52 (br, 3H), 2.57 (bs, 1H), 2.75–2.90 (br, 2H), 3.03 (bs, 1H), 3.12 (sept, 1H), 3.44 (bs, 1H), 3.72 (d, 1H), 4.11 (bs, 1H), 6.06 (d, 2H), 6.44 (s, 1H), 7.22 (d, 2H), 7.49 (s, 2H), 7.97 (d, 2H)

Example 48

Preparation of 3-n-heptanamido-4-i-propylbenzoic acid 4'-n-propylpiperazide ([1]-(16)-20)

To a solution of 3-amino-4-isopropylbenzoic acid 4'-n-propylpiperazide ([1]-(15)-20) (6.68 g) in pyridine (80 ml), enanthyl chloride (3.6 ml) was added dropwise under stirring while cooling on ice. The mixture was stirred for 1 hour while cooling on ice. The reaction solution was concentrated. The resulting yellow oil (10.61 g) was purified by silica gel column chromatography (Kieselgel 60, chloroform/methanol=15/1) to obtain the above-captioned compound ([1]-(15)-20) (8.94 g) as yellow oil.

$^1$H-NMR (500 MHz, CDCl$_3$) δ: 0.92 (t, 6H, J=7.3 Hz), 1.22 (d, 6H, J=6.9 Hz), 1.3–1.45 (m, 6H), 1.45–1.6 (b, 2H), 1.7–1.8 (m, 2H), 2.35–2.45 (m, 4H), 2.4–2.65 (b, 4H), 2.95–3.1 (m, 1H), 3.5–3.65 (b, 2H), 3.7–3.9 (b, 2H), 7.20 (d, 1H, J=7.8 Hz), 7.27 (d, 1H, J=7.8 Hz), 7.46 (s, 1H), 7.56 (s, 1H)

Example 49

Preparation of 3-N-[[(4-methoxycarbonylphenyl) methyl]n-heptanamido]4-i-propylbenzoic acid 4'-n-propyl piperazide ([1]-(17)-20')

Oily part of 60% sodium hydride (1.15 g) was washed with n-hexane, and suspended in THF (90 ml). To the suspension, a solution of the compound ([1]-(16)-20) (8.87 g) prepared in Example 48 in THF (90 ml) was added dropwise while cooling on ice. At the same temperature, a solution of methyl 4-bromo methylbenzoate (6.07 g) in THF (45 ml) was then added dropwise, and the mixture was stirred for 0.5 hour. After the mixture was further stirred at room temperature for 3 hours, the reaction solution was poured into water, and the whole was extracted with ethyl acetate. The ethyl acetate layer was washed with distilled water and saturated brine, dried over anhydrous sodium sulfate, filtered, and concentrated to obtain a yellowish brown solid (12.61 g). The crude solid was purified by silica gel column chromatography (Kieselgel 60, chloroform/methanol=50/1) to obtain the above-captioned compound ([1]-(17)-20') (8.96 g) as a colorless solid.

Melting point: 139°–141.0° C.

$^1$H-NMR (500 MHz, CDCl$_3$) δ: 0.84 (t, 3H, J=7.3 Hz), 0.91 (t, 3H, J=7.3 Hz), 1.15–1.3 (m, 6H), 1.19 (d, 3H, J=6.9 Hz), 1.20 (d, 3H, J=6.9 Hz), 1.47 (quint, 2H, J=7.3 Hz), 1.55–1.65 (m, 2H), 1.87–1.93 (m, 1H), 1.99–2.04 (m, 1H), 2.05–2.2 (b, 2H), 2.23–2.27 (m, 2H), 2.3–2.5 (b, 2H), 2.9–3.1 (b, 2H), 3.04 (quint, 1H, J=6.9 Hz), 3.6–3.75 (b, 2H), 3.90 (s, 3H), 3.98 (d, 1H, J=14.2 Hz), 5.73 (d, 1H, J=14.2 Hz), 6.59 (d, 1H, J=1.4 Hz), 7.28 (d, 2H, J=8.3 Hz), 7.42–7.46 (m, 2H), 7.93 (d, 2H, J=8.3 Hz)

Example 50

Preparation of 3-N-[[(4-carboxyphenyl)methyl]n-heptanamido]-4-i-propylbenzoic acid 4'-n-propylpiperazide ([1]-(17)-20) (Compound No. 20)

To a solution of the compound ([1]-(17)-20') (8.91 g) prepared in Example 49 in methanol (36 ml) and THF (36 ml), 1N NaOH aqueous solution (72 ml) was added, and the mixture was allowed to stand at room temperature for 3.5 hours. The reaction solution was neutralized with HCl, and concentrated. The residue was dissolved in chloroform. The chloroform layer was washed with distilled water and saturated brine, dried over anhydrous sodium sulfate, filtered, and concentrated to obtain yellow oil (12.35 g). The crude oil was purified by silica gel column chromatography (Kieselgel 60, chloroform/methanol=10/1) to obtain light yellow oil. The resulting oil was crystallized from n-hexane to obtain the above-captioned compound ([1]-(17)-20) (Compound No. 20) (8.32 g) as a colorless solid.

Melting point: 165.5°–168° C.

$^1$H-NMR (500 MHz, CDCl$_3$) δ: 0.84 (t, 3H, J=7.3 Hz), 0.91 (t, 3H, J=7.3 Hz), 1.15–1.3 (m, 6H), 1.23 (d, 3H, J=6.9 Hz), 1.35 (d, 3H, J=6.9 Hz), 1.55–1.7 (m, 4H), 1.85–1.95 (m, 1H), 2.0–2.1 (m, 1H), 2.1–2.25 (b, 1H), 2.4–2.7 (b, 4H), 2.7–2.9 (b, 2H), 3.0–3.15 (b, 1H), 3.14 (quint, 1H, J=6.9 Hz), 3.35–3.6 (b, 1H), 3.69 (d, 1H, J=14.2 Hz), 4.0–4.2 (b, 1H), 6.11 (d, 1H, J=14.2 Hz), 6.45 (s, 1H), 7.23 (d, 2H, J=8.3 Hz), 7.49–7.52 (m, 2H), 7.97 (d, 2H, J=8.3 Hz)

Example 51

Oral Absorption

Twelve-week-old Sprague-Dawley female rats (3 rats per group) were bred for acclimation for a week. Then, the compounds of the present invention and a reference substrate were dissolved in water, and orally administered to the rats in a single dosage (160 mg/kg). After 0.5 hour, 1 hour, 2 hours, 4 hours, 6 hours, 8 hours, and 24 hours, the amounts of each compound (ng) per 1 ml of serum were measured using HPLC. Curves were obtained from the relation between an elapsed time after administration and the amount of the compound in serum at each elapsed time, respectively, and an average of the areas under the curves was calculated. The results are shown in Table 2.

TABLE 2

| Compound No. | Area under curve (ng × hr/ml) |
|---|---|
| 1 | 13922 |
| 2 | 10689 |
| 3 | 9530 |
| 6 | 34679 |
| 7 | 13977 |
| 8 | 24558 |
| 9 | 50305 |
| 11 | 75977 |
| 12 | 32162 |
| 13 | 1456 |
| 15 | 5669 |
| 18 | 12760 |
| 19 | 172132 |
| 20 | 183106 |
| reference substance | 622 |

As a reference substance, Compound No. 184 disclosed in Japanese Unexamined Patent Publication (Kokai) No. 8-48651 was used. Compound No. 184 corresponds to the compound of the formula (I) wherein $R^1$=nBu, A=N, Z=C, $R^2$=CO, $R^3$=NC$_4$H$_8$O, $R^4$=H, $R^5$=Me, and $R^6$=Me.

Example 52

Acute Toxicity

Five-week-old ICR female mice (5 mice per group) were bred for acclimation for a week. Then, the compounds of the present invention were dissolved in water, and orally administered to the mice in a single dosage (500 mg/kg). The number of deaths was observed for 6 days after the administration. The results are shown in Table 3.

TABLE 3

| Compound No. | Number of deaths/number of survivals |
|---|---|
| 1 | 0/5 |
| 2 | 0/5 |
| 3 | 0/5 |
| 4 | 0/5 |
| 5 | 0/5 |
| 6 | 0/5 |
| 7 | 0/5 |
| 8 | 0/5 |
| 9 | 0/5 |
| 10 | 0/5 |
| 11 | 0/5 |
| 12 | 0/5 |
| 13 | 0/5 |
| 14 | 0/5 |
| 15 | 0/5 |

TABLE 3-continued

| Compound No. | Number of deaths/number of survivals |
| --- | --- |
| 16 | 0/5 |
| 17 | 0/5 |
| 18 | 0/5 |
| 19 | 0/5 |
| 20 | 0/5 |

Example 53

Binding to Receptors

In this Example, the affinity to the angiotensin II receptor subtype 1 or subtype 2 was evaluated by a binding assay in accordance with the method described in Biochem. Pharmacol., 33, 4057–4062 (1984).

Specifically, the measurement of the total binding in the presence of each drug was performed as follows:

A mixture (final volume=0.25 ml) of a drug in a given concentration (the drug was dissolved in DMSO, and diluted to a double volume with a buffer attached to a drug discovery system to prepare a sample for the assay; 0.025 ml), a tracer (0.025 ml), and receptors (0.2 ml) was incubated [in the case of the angiotensin II receptor subtype 1 ($AT_1$), at room temperature for 3 hours, and in the case of the subtype 2 ($AT_2$), at 37° C. for 1 hour]. Then, the reaction mixture was filtered with suction (GF/C filter was used in $AT_1$, and GF/B filter was used in $AT_2$). The filter papers after filtration with suction (the tracer bound to the receptors) were counted by a γ-well counter (ARC-500, Aloka). The non-specific bindings were measured by repeating the above method, except that a large excess amount of a displacer was added. The specific binding of the drug in the given concentration was calculated by subtracting the non-specific binding from the total binding, respectively.

In $AT_1$ and $AT_2$, the percentages found to inhibit the bindings of radioactive ligands (tracer) to receptors by the drugs to be tested ($IC_{50}$ value of concentration to show 50% inhibition, or binding inhibition % in 100 μM) were measured, using the drugs to be tested and control drugs in the given concentration. The results are shown in Table 4.

TABLE 4

| Compound No. | $IC_{50}$ $AT_1$ (nM) | Binding inhibition % in 100 μM $AT_1$ | $AT_2$ |
| --- | --- | --- | --- |
| 1 |  | 10 | 16 |
| 2 |  | 14 | 0 |
| 3 |  | 0 | 0 |
| 4 |  | 11 | 0 |
| 5 |  | 11 | 0 |
| 6 |  | 11 | 21 |
| 7 |  | 14 | 0 |
| 8 |  | 11 | 0 |
| 9 |  | 13 | 0 |
| 10 |  | 13 | 0 |
| 11 |  | 0 | 0 |
| 12 |  | 0 | 0 |
| 13 |  | 0 | 0 |
| 14 |  | 0 | 0 |
| 15 |  | 0 | 0 |
| 16 |  | 0 | 0 |
| 17 |  | 4 | 23 |
| 18 |  | 11 | 9 |
| 19 |  | 11 | 18 |
| 20 |  | 0 | 0 |
| DuP753 | 20 |  | 0 |

In $AT_1$,
receptor : from adrenal glands in rabbits
tracer : $^3$H-angiotensin II
control drug : DuP753
(displacer) : DuP753
In $AT_2$,
receptor : from cerebellar cortex in bovine
tracer : $^{125}$I-Tyr$^4$-angiotensin II
control drug : angiotensin II (human)
(displacer) : angiotensin II (human)

As clear from Table 4, the compounds of the present invention exhibit no inhibitory effect on the subtype 1 receptor. That the compounds of the present invention exhibit no binding activity to the subtype 1 receptor shows that such compounds have a completely different action mechanism from conventional ACE inhibitors or angiotensin II antagonists.

Example 54

Action to Lower Blood Pressure

The compounds of the present invention and the reference substance were administered with drinking water to kidney disease model rats, and the action of lowering the blood pressure was observed. The kidney disease model rats were prepared by a ligature of branches of renal artery in accordance with a conventional method. Namely, the left hilum renalis of Sprague-Dawley female rats was exposed under anesthesia, and one of four secondary branches of the renal artery was left unligated, while the remaining three branches were ligated, respectively. After a week, the hilum renalis (artery, vein, and ureter) of the right kidney were further ligated to thereby prepare rats whose renal function was lowered to approximately ⅛ of the normal function. Each group consisted of eight rats. The drugs to be tested (20 mg/kg) were administered to each administering group, and only water was administered to a control group. Two days after the administration, the systolic blood pressure was measured by the tail cuff method using a blood pressure measuring apparatus (UR5000; Ueda). The average of the blood pressures is shown in Table 5.

TABLE 5

| Compound No. | Blood Pressure (mmHg) |
| --- | --- |
| 1 | 205 |
| 2 | 200 |
| 3 | 203 |
| 4 | 204 |
| 5 | 200 |
| 6 | 209 |
| 7 | 206 |
| 8 | 203 |
| 9 | 207 |
| 10 | 206 |
| 11 | 204 |
| 12 | 202 |
| 13 | 208 |
| 14 | 205 |
| 15 | 200 |

TABLE 5-continued

| Compound No. | Blood Pressure (mmHg) |
|---|---|
| 16 | 202 |
| 17 | 201 |
| 18 | 210 |
| 19 | 194 |
| 20 | 209 |
| control | 210 |
| DuP753 | 130 |

In comparison with the control group, the reference substance (DuP753) clearly exhibited the action of lowering the blood pressure. On the contrary, an influence on the blood pressure was not substantially observed in the compounds of the present invention.

Example 55

Renal Function Indicatory Value (Action to Kidney Diseases)

The kidney disease model rats were prepared as in Example 54, and divided into twenty-two groups (8 rats per group) in a manner such that there were no major differences between each group in the serum creatinine value and the blood urea nitrogen value indicating renal function. The rats in each group were allowed to freely take up food. To the rats in the administering group, the compounds of the present invention or the reference substance (DuP753) were administered with drinking water at the dose of 20 mg/kg/day every day. To the rats in the control group, only water was administered every day. After six weeks, 0.2 ml of blood was collected from the carotid artery of the rats under anesthesia, and centrifuged to obtain serum. Using 25 μl of the serum, the serum creatinine (Scr) was measured by a creatinine analytical instrument (Beckman). Using 10 μl of the serum, the blood urea nitrogen (BUN) was measured by a BUN analytical instrument (Beckman). The creatinine clearance was evaluated as follows:

After the serum creatinine measurement, rats were placed in urinary metabolic cages for 24 hours to collect urine. A urinary creatine concentration (Ucr) was measured by a creatinine analytical instrument, and a total volume of urination (Uvol) was also measured. The creatinine clearance (CCr) was calculated by the following formula:

$$CCr(\text{ml/min}) = \frac{Ucr(\text{mg/dl}) \times Uvol(\text{ml})}{Scr(\text{mg/dl}) \times 24 \times 60(\text{min})}$$

The results are shown in Table 6.

TABLE 6

| Compound No. | Creatinine mg/dl | Blood urea nitrogen mg/dl | Creatinine clearance ml/min |
|---|---|---|---|
| 1 | 1.2 | 62 | 0.47 |
| 2 | 1.3 | 78 | 0.33 |
| 3 | 1.3 | 78 | 0.33 |
| 4 | 1.4 | 72 | 0.37 |
| 5 | 1.6 | 82 | 0.30 |
| 6 | 1.3 | 75 | 0.33 |
| 7 | 1.4 | 76 | 0.32 |
| 8 | 1.5 | 78 | 0.35 |
| 9 | 1.6 | 83 | 0.31 |
| 10 | 1.6 | 81 | 0.32 |
| 11 | 1.2 | 62 | 0.42 |
| 12 | 1.3 | 80 | 0.35 |
| 13 | 1.5 | 77 | 0.32 |
| 14 | 1.7 | 86 | 0.27 |
| 15 | 1.8 | 90 | 0.26 |
| 16 | 1.5 | 78 | 0.33 |
| 17 | 1.5 | 78 | 0.33 |
| 18 | 1.4 | 76 | 0.32 |
| 19 | 1.3 | 76 | 0.33 |
| 20 | 1.3 | 75 | 0.32 |
| control | 2.0 | 100 | 0.22 |
| DuP753 | 1.6 | 80 | 0.32 |

When the compounds of the present invention were administered, the serum creatinine value and the blood urea nitrogen value, which increase with an aggravation of renal failure, clearly became lower values, and the creatinine clearance indicating renal function was clearly improved in comparison with the control substance. The pharmacological effects were comparable or superior to those of the reference substance, and it was shown that the compounds of the present invention do not substantially exhibit a conventional angiotensin II receptor antagonism and blood pressure lowering action, but alleviate kidney diseases.

Example 56

Action to Survival Time of Kidney Diseased Animals

The kidney disease model rats were prepared as in Example 54. Twenty-two groups (8 rats per group) were prepared in a manner such that there was no major difference between the groups in the serum creatinine value and the blood urea nitrogen value indicating renal function. The rats in each group were allowed to freely take up food. To the rats in the administering group, the compounds of the present invention or the reference substance (DuP753) were administered with drinking water at the dose of 20 mg/kg/day every day. To the rats in the control group, only water was administered every day. If kidney diseases are aggravated, the rat will die of uremia. Thus, the survival time was observed as a comprehensive indication of the improvement of the effect on the kidney diseases. The results are shown in Table 7. The observation period was eight weeks. Thus if all rats survived, the average survival time is eight weeks, and is an upper limit.

TABLE 7

| Compound No. | Average survival time (weeks) |
|---|---|
| 1 | 7.5 |
| 2 | 6.9 |
| 3 | 6.9 |
| 4 | 6.9 |
| 5 | 6.9 |
| 6 | 7.0 |
| 7 | 6.9 |
| 8 | 6.9 |
| 9 | 6.9 |
| 10 | 6.9 |
| 11 | 7.3 |
| 12 | 7.0 |
| 13 | 6.9 |

TABLE 7-continued

| Compound No. | Average survival time (weeks) |
| --- | --- |
| 14 | 6.3 |
| 15 | 6.1 |
| 16 | 6.9 |
| 17 | 6.9 |
| 18 | 7.0 |
| 19 | 7.2 |
| 20 | 7.3 |
| control | 5.0 |
| DuP753 | 6.9 |

The compounds of the present invention clearly prolonged the survival time of the kidney disease model rats. The effect was comparable or superior to that of the reference substance. It was shown that the compounds of this invention do not substantially exhibit known angiotensin II receptor antagonism and blood pressure lowering action, but prolonged the survival time of the rats having kidney diseases.

Although the present invention has been described with reference to specific embodiments, various changes and modifications obvious to those skilled in the art are deemed to be within the spirit, scope, and concept of the invention.

We claim:

1. An aromatic compound of the formula (I):

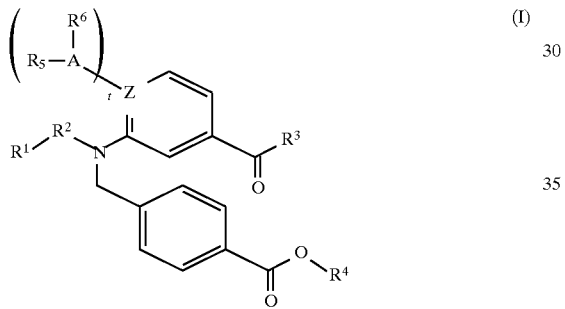

wherein $R^1$ is a hydrogen atom, an alkyl of 1 to 8 carbon atoms, a haloalkyl of 1 to 8 carbon atoms, or —$NR^7R^8$; $R^2$ is —C(=O)— or a single bond; $R^3$ is —$OR^9$, a three- to seven-membered saturated cycloaliphatic amino group which may be interrupted by one or more nitrogen, oxygen, or sulfur atoms, a three- to seven-membered saturated cycloaliphatic amino group containing at least one nitrogen atom in the ring which is substituted with one or more alkyl groups of 1 to 8 carbon atoms or one or more haloalkyl groups of 1 to 8 carbon atoms, a three- to seven-membered saturated cycloaliphatic alkyl group containing at least one nitrogen atom in the ring which may be substituted with one or more alkyl groups of 1 to 8 carbon atoms or one or more haloalkyl groups of 1 to 8 carbon atoms, or —$NR^{10}R^{11}$;

$R^4$ is a hydrogen atom, an alkyl of 1 to 8 carbon atoms, a haloalkyl of 1 to 8 carbon atoms, —$(CH_2)_mNR^{12}R^{13}$, —$(CH_2)_nR^{14}$, —$(CH_2)_pCH(NR^{15}R^{16})COOR^{17}$, —$R^{18}$—$COOR^{19}$, —$CH(R^{20})OC(=O)OR^{21}$, or —$CH(R^{22})OC(=O)R^{23}$; $R^{10}$ and $R^{11}$ are independently a hydrogen atom, an alkyl of 1 to 8 carbon atoms, a haloalkyl of 1 to 8 carbon atoms, or —$(CH_2)_qNR^{24}R^{25}$; $R^{14}$ is a three- to seven-membered saturated cycloaliphatic amino group which may be interrupted by one or more nitrogen, oxygen, or sulfur atoms, a three- to seven-membered saturated cycloaliphatic amino group containing at least one nitrogen atom in the ring which is substituted with one or more alkyl groups of 1 to 8 carbon atoms or one or more haloalkyl groups of 1 to 8 carbon atoms, a three- to seven-membered saturated cycloaliphatic alkyl group containing at least one nitrogen atom in the ring which may be substituted with one or more alkyl groups of 1 to 8 carbon atoms or one or more haloalkyl groups of 1 to 8 carbon atoms, or a three- to seven-membered unsaturated heterocyclic group; $R^{18}$ is a three- to seven-membered saturated cycloaliphatic alkylene group containing at least one nitrogen atom in the ring which may be substituted with one or more alkyl groups of 1 to 8 carbon atoms or one or more haloalkyl groups of 1 to 8 carbon atoms; $R^{21}$ and $R^{23}$ are —$(CH_2)_rR^{26}$; $R^{26}$ is a hydrogen atom, an alkyl of 1 to 8 carbon atoms, a haloalkyl of 1 to 8 carbon atoms, —$NR^{27}R^{28}$, or a three- to eight-membered saturated cycloaliphatic alkyl group; Z is C, CH, or N; A is CH or N; $R^5$, $R^6$, $R^7$, $R^8$, $R^9$, $R^{12}$, $R^{13}$, $R^{15}$, $R^{16}$, $R^{17}$, $R^{19}$, $R^{20}$, $R^{22}$, $R^{24}$, $R^{25}$, $R^{27}$, and $R^{28}$ are independently a hydrogen atom, an alkyl of 1 to 8 carbon atoms, or a haloalkyl of 1 to 8 carbon atoms; t is 0 or 1; and m, n, p, q, and r are independently 0 or an integer of 1 to 6, with the proviso that when $R^4$ is a hydrogen atom, an alkyl of 1 to 8 carbon atoms, or a haloalkyl of 1 to 8 carbon atoms, $R^3$ is a three- to seven-membered saturated cycloaliphatic amino group containing at least one nitrogen atom in the ring which is substituted with one or more alkyl groups of 1 to 8 carbon atoms or one or more haloalkyl groups of 1 to 8 carbon atoms, a three- to seven-membered saturated cycloaliphatic alkyl group containing at least one nitrogen atom in the ring which may be substituted with one or more alkyl groups of 1 to 8 carbon atoms or one or more haloalkyl groups of 1 to 8 carbon atoms, or —$NR^{10}R^{11}$ wherein at least one of $R^{10}$ and $R^{11}$ is —$(CH_2)_qNR^{24}R^{25}$, or a salt thereof.

2. An aromatic compound according to claim 1, wherein $R^1$ is a hydrogen atom, an alkyl of 1 to 8 carbon atoms, a haloalkyl of 1 to 8 carbon atoms, or —$NR^7R^8$; $R^2$ is —C(=O)— or single bond; $R^3$ is —$OR^9$, a three- to six-membered saturated cycloaliphatic amino group which may be interrupted by one or more nitrogen, oxygen, or sulfur atoms, a three- to six--membered saturated cycloaliphatic amino group containing at least one nitrogen atom in the ring which is substituted with one or more alkyl groups of 1 to 6 carbon atoms or one or more haloalkyl groups of 1 to 6 carbon atoms, a three- to six-membered saturated cycloaliphatic alkyl group containing at least one nitrogen atom in the ring which may be substituted with one or more alkyl groups of 1 to 6 carbon atoms or one or more haloalkyl groups of 1 to 6 carbon atoms, or —$NR^{10}R^{11}$; $R^4$ is a hydrogen atom, an alkyl of 1 to 5 carbon atoms, a haloalkyl of 1 to 5 carbon atoms, —$(CH_2)_mNR^{12}R^{13}$, —$(CH_2)_nR^{14}$, —$(CH_2)_pCH(NR^{15}R^{16})COOR^{17}$, —$R^{18}$—$COOR^{19}$, —$CH(R^{20})OC(=O)OR^{21}$, or —$CH(R^{22})OC(=O)R^{23}$; $R^{10}$ and $R^{11}$ is independently a hydrogen atom, an alkyl of 1 to 5 carbon atoms, a haloalkyl of 1 to 5 carbon atoms, or —$(CH_2)_qNR^{24}R^{25}$; $R^{14}$ is a three- to six-membered saturated cycloaliphatic amino group which may be interrupted by one or more nitrogen, oxygen, or sulfur atoms, a three- to six-membered saturated cycloaliphatic amino group containing at least one nitrogen atom in the ring which is substituted with one or more alkyl groups of 1 to 6 carbon atoms or one or more haloalkyl groups of 1 to 6 carbon atoms, a three- to six-membered saturated cycloaliphatic alkyl group containing at least one nitrogen atom in the ring which may be substituted with one or more alkyl groups of 1 to 6 carbon atoms or one or more haloalkyl groups of 1 to 6 carbon atoms, or a three- to six-membered unsaturated heterocyclic group; $R^{18}$ is a three- to six-membered saturated cycloaliphatic alkylene group containing at least one nitrogen atom in the ring which may be substituted with one or more alkyl groups of 1 to 6 carbon atoms or one or more haloalkyl groups of 1 to 6 carbon atoms; $R^{21}$ and $R^{23}$ is $-(CH_2)_rR^{26}$; $R^{26}$ is a hydrogen atom, an alkyl of 1 to 5 carbon atoms, a haloalkyl of 1 to 5 carbon atoms, $-NR^{27}R^{28}$, or a three- to six-membered saturated cycloaliphatic alkyl group; Z is C, CH, or N; A is CH or N; $R^5$, $R^6$, $R^7$, $R^8$, $R^9$, $R^{12}$, $R^{13}$, $R^{15}$, $R^{16}$, $R^{17}$, $R^{19}$, $R^{20}$, $R^{22}$, $R^{24}$, $R^{25}$, $R^{27}$, and $R^{28}$ are independently a hydrogen atom, an alkyl of 1 to 5 carbon atoms, or a haloalkyl of 1 to 5 carbon atoms; m, n, p, q, and r is independently 0 or an integer of 1 to 4, with the proviso that when $R^4$ is a hydrogen atom, an alkyl of 1 to 5 carbon atoms, or a haloalkyl of 1 to 5 carbon atoms, $R^3$ is a three- to six-membered saturated cycloaliphatic amino group containing at least one nitrogen atom in the ring which is substituted with one or more alkyl groups of 1 to 6 carbon atoms or one or more haloalkyl groups of 1 to 6 carbon atoms, a three- to six-membered saturated cycloaliphatic alkyl group containing at least one nitrogen atom in the ring which may be substituted with one or more alkyl groups of 1 to 6 carbon atoms or one or more haloalkyl groups of 1 to 6 carbon atoms, or $-NR^{10}R^{11}$ wherein at least one of $R^{10}$ and $R^{11}$ is $-(CH_2)_qNR^{24}R^{25}$, or a salt thereof.

3. An aromatic compound according to claim 1, wherein $R^3$ is a three- to six-membered saturated cycloaliphatic amino group containing at least one nitrogen atom in the ring which is substituted with one or more alkyl groups of 1 to 6 carbon atoms or one or more haloalkyl groups of 1 to 6 carbon atoms, a three- to six-membered saturated cycloaliphatic alkyl group containing at least one nitrogen atom in the ring which may be substituted with one or more alkyl groups of 1 to 6 carbon atoms or one or more haloalkyl groups of 1 to 6 carbon atoms, or $-NR^{10}R^{11}$ wherein at least one of $R^{10}$ and $R^{11}$ is $-(CH_2)_qNR^{24}R^{25}$, or a salt thereof.

4. An aromatic compound according to claim 1, wherein $R^4$ is $-(CH_2)_mNR^{12}R^{13}$, $-(CH_2)_nR^{14}$, $-(CH_2)_pCH(NR^{15}R^{16})COOR^{17}$, $-R^{18}-COOR^{19}$, $-CH(R^{20})OC(=O)OR^{21}$, or $-CH(R^{22})OC(=O)R^{23}$, or a salt thereof.

5. A pharmaceutical composition comprising an aromatic compound of the formula (I) according to claim 1 or a pharmaceutically acceptable salt thereof, and a pharmaceutically acceptable carrier or diluent.

6. A pharmaceutical composition according to claim 5, wherein the pharmaceutically acceptable salt is an acid additive salt.

7. A pharmaceutical composition according to claim 5, which is an agent for treating kidney diseases.

8. A method for treating kidney diseases, comprising administering to a mammal in need thereof an effective amount of an aromatic compound of the formula (I) according to claim 1 or a pharmaceutically acceptable salt thereof.

9. The method according to claim 8, wherein said kidney disease is selected from the group consisting of nephritis, nephropathy, renal failure, nephrotic syndrome, asymptomatic proteinuria, hematuria, diabetic nephropathy, kidney diseases induced by medicine, urinary tract infectious diseases and prostatitis.

\* \* \* \* \*